United States Patent
Suzuki et al.

(10) Patent No.: US 7,109,043 B2
(45) Date of Patent: Sep. 19, 2006

(54) FLUORESCENT PROBE FOR MAGNESIUM ION DETERMINATION

(75) Inventors: Koji Suzuki, Kawasaki (JP); Yoshio Suzuki, Yokohama (JP); Kotaro Oka, Sagamihara (JP)

(73) Assignees: Japan Science and Technology Corporation, Kawaguchi (JP); The Kanagawa Academy of Science and Technology Foundation, Kawasaki (JP); Keio University, Tokyo (JP)

( * ) Notice: Subject to any disclaimer, the term of this patent is extended or adjusted under 35 U.S.C. 154(b) by 286 days.

(21) Appl. No.: 10/333,976

(22) PCT Filed: Jul. 25, 2001

(86) PCT No.: PCT/JP01/06401

§ 371 (c)(1),
(2), (4) Date: Jul. 18, 2003

(87) PCT Pub. No.: WO02/12867

PCT Pub. Date: Feb. 14, 2002

(65) Prior Publication Data

US 2004/0044228 A1 Mar. 4, 2004

(30) Foreign Application Priority Data

Jul. 28, 2000 (JP) ............................. 2000-228489

(51) Int. Cl.
*G01N 33/533* (2006.01)
*G01N 21/76* (2006.01)
*G01N 33/30* (2006.01)
*C12P 7/26* (2006.01)
*C07D 311/46* (2006.01)

(52) U.S. Cl. .................. 436/546; 436/172; 436/79; 436/128; 435/148; 435/968; 549/285; 546/47; 546/49; 536/4.1

(58) Field of Classification Search ............ 436/546, 436/172, 79, 128; 546/47, 49; 549/285; 536/4.1; 435/148, 968
See application file for complete search history.

(56) References Cited

U.S. PATENT DOCUMENTS 5,631,169 A * 5/1997 Lakowicz et al. .......... 436/537

FOREIGN PATENT DOCUMENTS

| EP | 397641 A2 | * | 11/1990 |
| JP | 58-53758 A | | 3/1983 |
| JP | 62-261063 A | | 11/1987 |
| JP | 4-120464 A | | 4/1992 |
| JP | 2000252069 A | * | 9/2000 |

OTHER PUBLICATIONS

Ahmed et al. Preparation of 3-substituted 6,7-dimethoxyquinoxalin-2(1H)-ones and studies of their potential as fluorophores. 1995 Tetrahedron, vol. 51, No. 47, pp. 12899-12910.*
Mori Y, Single-layer organic electroluminescent devices, HCAPLUS Abstract, Organic electoluminescent materials and devices, Conference 1997, Gordon and Breach:Amsterdam, Neth.*
Wolfbeis et al. Fluorophore-chromophore spectrochemical method for determining a chemical parameter of a sample. CAPLUS search documen related to EP 397641 A2, 1990.*
Chapman, Curtis F., et al. The Journal of Physical Chemistry, vol. 95, pp. 9095-9114, 1991.

* cited by examiner

*Primary Examiner*—Long V. Le
*Assistant Examiner*—Shafiqul Haq
(74) *Attorney, Agent, or Firm*—Birch, Stewart, Kolasch & Birch, LLP

(57) ABSTRACT

A fluorescent probe for measuring magnesium ion, which can selectively form a complex with magnesium ion in aqueous system is disclosed. The fluorescent probe for measuring magnesium ion according to the present invention has the structure represented by the following Formula [I]:

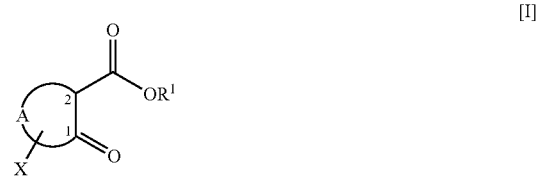

(wherein $R^1$ represents a hydrogen atom, metal atom or an ester-forming group; A represents a group which forms a ring structure together with carbon atom 1 and carbon atom 2; and X is a fluorescent group which may form a condensed ring together with the ring containing the group A).

20 Claims, 1 Drawing Sheet

FLUORESCENT PROBE FOR MAGNESIUM ION DETERMINATION

This application is the national phase under 35 U.S.C. § 371 of PCT International Application No. PCT/JP01/06401 which has an International filing date of Jul. 25, 2001, which designated the United States of America.

TECHNICAL FIELD

The present invention relates to a fluorescent probe for measuring magnesium ion existing in solutions.

BACKGROUND ART

Methods for quantifying magnesium ion in a sample includes a method using an ion-selective electrode, and atomic absorption method. Ion-selective electrode is a sensor which selectively responds to the target ion and converts the response to electrochemical information, and the ion activity is determined from the response potential. Atomic absorption method is a method in which vaporized metal atoms are irradiated with a light having a specific wavelength and the metal atoms are quantified from the amount of the absorption. Both of these methods have good sensitivity and accuracy. However, it is pointed out that these methods require pretreatment, and real time monitoring cannot be carried out.

On the other hand, similar to the above-mentioned atomic absorption method, methods for quantifying the target substance in a sample utilizing the process of absorption of light or emission of light by the substance are now rapidly developing with the development of spectroscopy. Among these, fluorometry is now widely used as one of the methods enabling trace of kinetic behavior of metal ions in the body, because the pretreatment is simple, real-time measurement can be attained, and because of the rapid progress of the measuring apparatuses such as fluorescence microscope and confocal laser microscope. Particularly, fluorescent probes for measuring calcium ion have the largest share in this field, and a number of calcium ion-selective fluorescent probes have been synthesized. By virtue of these probes, the kinetic behaviors of magnesium ions in the cells of nerve, muscle and organs are imaged, and so the probes greatly contribute to the fields of medicine and biology.

Magnesium ion is an important metal ion in the body, which acts as a buffering agent, and which controls enzyme reactions and photosynthesis reactions in green plants. In case of the above-mentioned calcium ion, a wide variety of fluorescent pigment molecules have been developed and the behaviors of calcium ions in the body have been clarified. In contrast, no effective fluorescent probe for magnesium ion has been developed. The reasons therefor include that the hydration energy of magnesium ion is greater than that of calcium ion so that a large binding constant cannot be obtained in water, and that competition reaction by calcium ions occurs, so that a complex cannot be formed selectively with magnesium ion.

DISCLOSURE OF THE INVENTION

Accordingly, an object of the present invention is to provide a fluorescent probe for measuring magnesium ion, which can selectively form a complex with magnesium ion in aqueous system.

The present inventors intensively studied to discover that β-diketone structure on a cyclic structure selectively forms a complex with magnesium ion in aqueous system, and to experimentally confirm that a fluorescent molecule having the above-mentioned structure may be used as a fluorescent probe selective for magnesium ion, thereby completing the present invention.

That is, the present invention provides a fluorescent probe for measuring magnesium ion, which has the structure represented by the following Formula [I]:

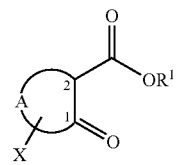

[I]

(wherein $R^1$ represents a hydrogen atom, metal atom or an ester-forming group; A represents a group which forms a ring structure together with carbon atom 1 and carbon atom 2; and X is a fluorescent group which may form a condensed ring together with said ring containing said group A).

The present invention also provides a use of the compound represented by the above-described Formula [I] for the production of a fluorescent probe for measuring magnesium ion. The present invention further provides a method for measuring magnesium ion in a sample, comprising contacting said fluorescent probe according to the present invention with the sample containing magnesium ions; and measuring the fluorescence from said fluorescent probe bound to the magnesium ion in said sample.

By the present invention, a selective fluorescent probe for measuring magnesium ion, which can selectively form a complex with magnesium ion in aqueous system even in the presence of calcium ions, was first provided. It is thought that the fluorescent probe according to the present invention will much contribute to the analysis of behavior of magnesium ions in the body or the like.

BEST MODE FOR CARRYING OUT THE INVENTION

Figure 1:
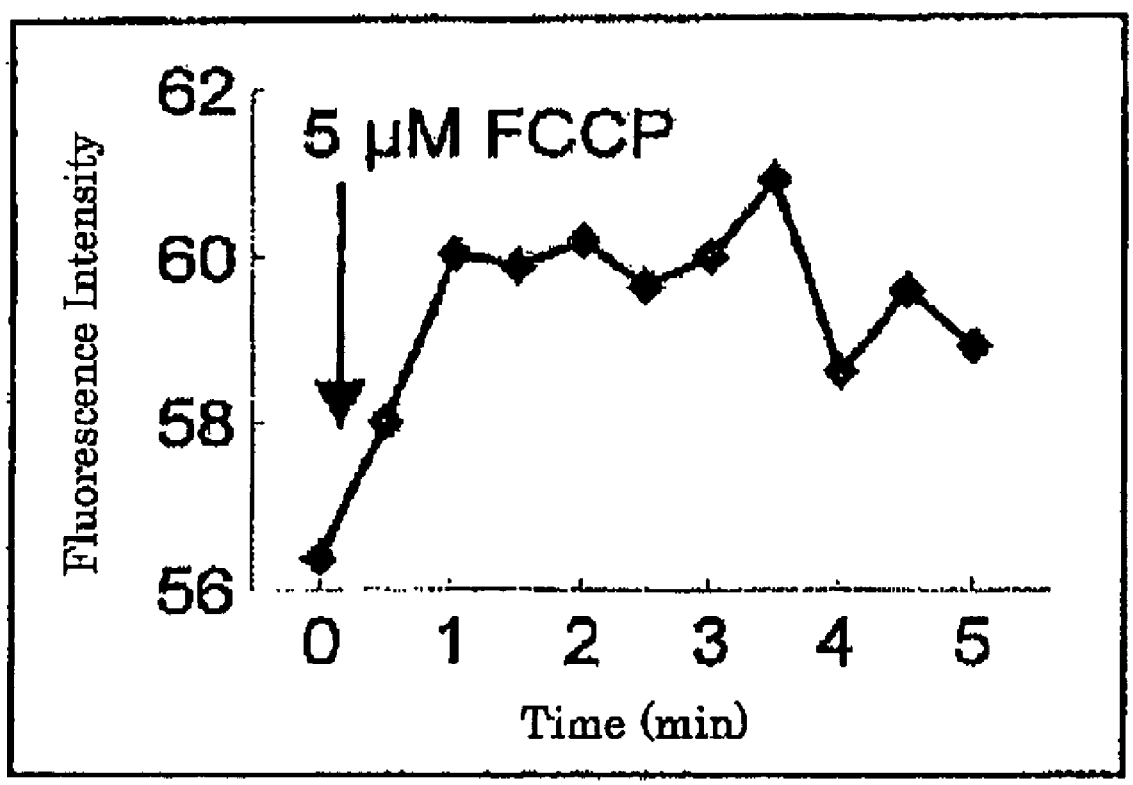
FIG. 1 shows the relationship between the time (minutes) after addition of FCCP which was added after addition of a fluorescent probe KMG-20 synthesized in Example 1 of the present invention and the fluorescence intensity of the image of fluorescent microscope of vascular endothelial cells.

The present invention is based on the discovery that β-diketone structure on a cyclic structure selectively forms a complex with magnesium ion in aqueous system even in the presence of calcium ions. The term "β-diketone structure" herein means the structure wherein two carbonyl groups are bound through a methylene group. If β-diketone structure exists in a molecule, magnesium ion is selectively chelated by the β-diketone structure in aqueous system. Therefore, if the molecule is fluorescent, the molecule may be used as a magnesium ion-selective probe. Thus, any molecule having the β-diketone structure on a cyclic structure and an optional fluorescent group may be used as the probe for selectively measuring magnesium ion, and is within the scope of the present invention. That is, the fluorescent probe according to the present invention is represented by the above-described Formula [I].

In general, since fluorescence emitted by a fluorescent group changes (increased or decreased) by the formation of a complex between the molecule and a metal, the magnesium ion may be measured based on this change. Even in cases where the fluorescence characteristics are not substantially changed by the formation of the complex, magnesium ion may be measured by removing the unbound probe from the sample. In the present specification, the term "measure" includes both quantification and detection.

In the above-described Formula [I], $R^1$ represents a hydrogen atom, metal atom or an ester-forming group. In cases where $R^1$ is a metal atom, the metal ion electrolytically dissociate to yield COO$^-$ group, and this COO$^-$ group plays a role in chelating the magnesium ion. Therefore, $R^1$ may be an arbitrary metal atom, and examples thereof include monovalent metal atoms such as alkaline metals such as sodium and potassium. The term "ester-forming group" means the $R^1$ which forms an ester with the carboxyl group to constitute the ester structure represented by COOR$^1$. Since the ester bond in the structure COOR$^1$ is cleaved in the body by the action of an esterase to yield COO$^-$, and this COO$^-$ group plays a role in chelating the magnesium ion, $R^1$ is not at all limited and may be an arbitrary group.

In cases where a probe has the structure represented by Formula [I], the probe can more accurately chelate the magnesium ion because the β-diketone structure is firmly supported by the cyclic structure. Since the cyclic structure containing A may be any cyclic structure as long as it supports the βdiketone structure on the cyclic structure, the cyclic structure per se is not restricted at all. Usually, the cyclic structure is a 5- to 7-membered ring, and may be an aromatic ring such as benzene ring, or may be a structure such as cycloalkyl which may contain (a) double bond(s), or may be a hetero ring. With the structure of Formula [I], since one of the carbonyl groups is derived from a carboxyl group, $R^1$ may be arbitrarily selected. For example, for measuring magnesium ion in the cells, a structure which makes it easier for the probe to pass through the cell membrane may be employed. As an example of the structure which makes it easier for the probe to pass through the cell membrane, the structure represented by Formula [IX] below may be cited.

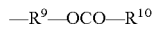   [IX]

(wherein $R^9$ represents $C_1$–$C_4$ alkylene, and $R^{10}$ represents $C_1$–$C_4$ alkyl). In the present specification, "alkyl group" includes both linear alkyl groups and branched alkyl groups. In Formula [IX], the smaller the number of carbon atoms in $R^9$ and $R^{10}$, the better. Therefore, the most preferred $R^9$ is methylene group, and the most preferred $R^{10}$ is methyl group. The above-described explanation about $R^1$ is applied to $R^1$ in Formulae [II], [III], [IV], [V], [VII], [VIII], [X], [XIII], [XIV], [XV] and [XVI].

The fluorescent group represented by X in Formula [I] may be an arbitrary fluorescent group. For example, various fluorescent probes for measuring calcium ion are known, and any of the fluorescent groups employed in these fluorescent probes may be employed in the present invention. Examples of such fluorescent groups include Rhodamine, fluorescein, naphthalene, anthracene, pyrene, coumarin, quinoline, stilbene, benzothiazole and pyrazoline.

Among the structures represented by Formula [I], those represented by the following Formula [II] are preferred in view of sensitivity.

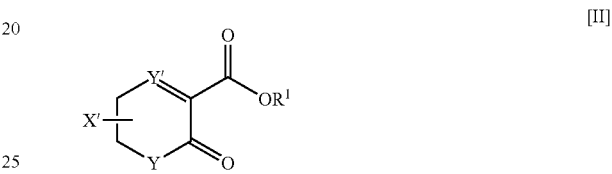   [II]

(wherein $R^1$ represents the same meaning as in Formula [I]; Y represents —O—, —CH$_2$— or —NH—; Y' represents —CH= or —N=; X' represents a fluorescent group which may form a condensed ring together with carbon atom 3 and carbon atom 4; each hydrogen atom bound to arbitrary one or more carbon atoms constituting the ring structure in Formula [II] may be substituted by $C_1$–$C_6$ alkyl, $C_1$–$C_6$ alkoxyl, amino, halogen or nitro). In the present specification, as the "halogen", fluorine, chlorine, bromine and iodine are preferred.

In Formula [II], Y' is preferably —CH=, and Y is preferably —O—. Each of the hydrogen atoms bound to the carbon atoms constituting the ring may be substituted as described above. However, since such a substituent is not necessary, the non-substituted ring is preferred because it is simple. As X', various known fluorescent groups may preferably be employed.

Among the structures represented by Formula [II], coumarin derivatives represented by Formula [III] are especially preferred.

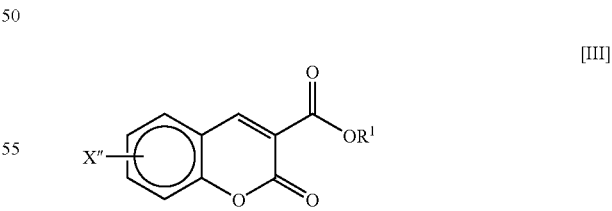   [III]

(wherein $R^1$ represents the same meaning as in Formula [I]; X" is a fluorescent group which may be a ring condensed with the benzene ring shown in the formula; each hydrogen atom bound to arbitrary one or more carbon atoms constituting the ring structure in Formula [III] may be substituted by $C_1$–$C_6$ alkyl, $C_1$–$C_6$ alkoxyl, amino, mono- or dialkylamino in which each alkyl group has 1 to 6 carbon atoms, halogen or nitro).

In the structure represented by Formula [III], each of the hydrogen atoms bound to the carbon atoms constituting the ring may be substituted as described above. However, since such a substituent is not necessary, the non-substituted structures are preferred because of simplicity. As X", known various fluorescent groups may preferably be employed.

Among the structures represented by Formula [III], preferred examples include those wherein the condensed benzene ring in the coumarin moiety is further condensed to form a structure containing totally 3 to 5 condensed rings. Examples of such preferred structures include the structures represented by the following Formulae [IV] and [V].

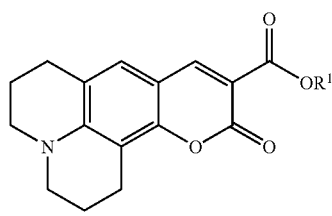

[IV]

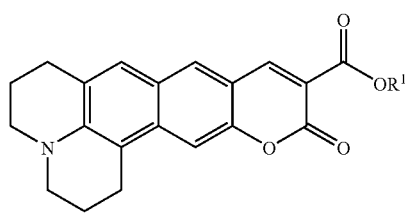

[V]

In Formulae [IV] and [V], $R^1$ represents the same meaning as in Formula [I]; each hydrogen atom bound to arbitrary one or more carbon atoms constituting the ring structure in Formula [V] may be substituted by $C_1$–$C_6$ alkyl, $C_1$–$C_6$ alkoxyl, amino, mono- or dialkylamino in which each alkyl group has 1 to 6 carbon atoms, halogen or nitro. However, as mentioned above, these substituents are not necessary, and those having no such substituents are preferred. The structure represented by Formula [V] is one wherein one condensed benzene ring having conjugated double bonds is added to the structure represented by Formula [IV], so that the number of conjugated double bonds is larger than in the structure represented by Formula [IV]. Therefore, excitation may be carried out at a longer wavelength than that employed for the excitation of the structure represented by Formula [IV], and may be observed with a laser microscope using an excitation light having a wavelength of about 488 nm. Therefore, it is especially advantageous for the purpose of observing the behavior of magnesium ions in the cells, or the like.

As preferred fluorescent probes according to the present invention, which are excellent in the ability to form a complex with magnesium ion, and in the optical characteristics such as absorption spectrum and fluorescence spectrum, which attain uniform staining when added to cells, and which have large fluorescence intensities, the compounds represented by Formula [XIII] below are cited.

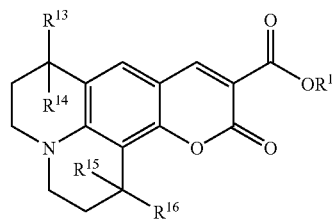

[XIII]

(wherein $R^1$ represents the same meaning as in Formula [I]; and $R^{13}$, $R^{14}$, $R^{15}$ and $R^{16}$ independently represent hydrogen, $C_1$–$C_5$ alkyl or halogen (excluding the cases wherein $R^{13}$, $R^{14}$, $R^{15}$ and $R^{16}$ are simultaneously hydrogen atoms).

Among the compounds represented by Formula [XIII], those wherein $R^{13}$, $R^{14}$, $R^{15}$ and $R^{16}$ are $C_1$–$C_5$ alkyl are preferred. Especially, it was found that the compound (KMG-27) wherein all of $R^{13}$, $R^{14}$, $R^{15}$ and $R^{16}$ are methyl has the characteristics (complex-forming ability, optical characteristics and uniformity in staining when added to cells) of KMG-20 which is a preferred compound according to the present invention prepared in Example 1 below, and that this compound gives a larger fluorescence intensity (brighter) than KMG-20. Further, it was observed that when added to cells, the compound was uniformly dispersed in the cells similar to KMG-20, and increase in the fluorescent intensity was observed when a stimulant which increases the magnesium ion level was added.

With the compounds represented by Formula [XIII], by using a confocal laser scanning microscope having a 452 nm Ar laser, when the object to be observed is a cell, three-dimensional information of the cell may be obtained.

As the preferred fluorescent probes according to the present invention having high water solubilities, the compounds represented by the following Formula [XIV] are cited.

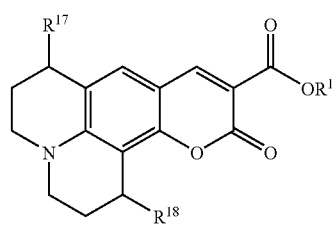

[XIV]

(wherein $R^1$ represents the same meaning as in Formula [I]; and $R^{17}$ and $R^{18}$ independently represent hydrogen, hydroxyl, halogen, carboxyl or —COOR$^{19}$ (wherein $R^{19}$ represents a monovalent metal ion) (excluding the cases wherein $R^{17}$ and $R^{18}$ are simultaneously hydrogen atoms).

As the monovalent metal ion, an alkaline metal such as sodium or potassium is preferred. Both of $R^{17}$ and $R^{18}$ are preferably the above-described groups other than hydrogen atoms, and those wherein both of them are hydroxyl groups are especially preferred. Modification of hydroxyl group is easy and various organic synthesis methods therefor have been established. Therefore, the compounds may be used not only as the compounds having higher water solubilities than KMG-20, but also may be used as reaction intermediates for synthesizing better compounds than KMG-20.

Since the compounds represented by Formula [XIV] have higher water solubilities, a dispersed state of the reagent in a cell, which is different from that of KMG-20 or the like is expected.

With the compounds represented by Formula [XIV], by using a confocal laser scanning microscope having a 452 nm Ar laser, when the object to be observed is a cell, three-dimensional information of the cell may be obtained.

As the preferred fluorescent probes according to the present invention, of which absorption bands are within the longer wavelength ranges, the compounds represented by the following Formula [XV] are cited.

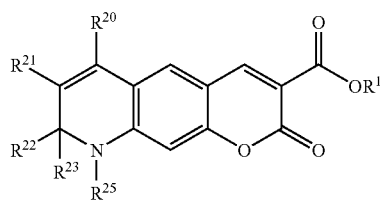

[XV]

(wherein $R^1$ represents the same meaning as in Formula [I]; and $R^{20}$, $R^{21}$, $R^{22}$, $R^{23}$, $R^{24}$ and $R^{25}$ independently represent hydrogen, $C_1$–$C_5$ alkyl, halogen or hydroxyl).

In the compounds represented by Formula [XV], the carbon atom to which $R^{20}$ is bound and the carbon atom to which $R^{21}$ is bound are bonded by double bond, and their absorption bands are within longer wavelength ranges than that of KMG-20 because of this double bond. Therefore, it may be excited with an Ar laser having a wavelength of 488 nm which is more widely used, and their complex-forming abilities, optical characteristics, and uniformity of staining when added to cells are good.

Among the compounds represented by Formula [III], preferred examples are those wherein the symbol X" in Formula [III] is represented by the Formula [VI]:

X'''-Z- [VI]

(wherein X''' represents a fluorescent group having a condensed ring containing 2 to 4 rings; -Z- represents a group which binds the fluorescent group and the benzene ring shown in Formula [III]).

Examples of X''' include various known fluorescent groups such as Rhodamine and fluorescein. Since -Z- is nothing more than a structure merely binding the coumarin structure and the fluorescent group, it is not restricted at all, and may be, for example, $C_1$–$C_4$ lower alkylene group. To increase the hydrophilicity, however, structures containing a polar group such as amine, carbonyl group, thiocarbonyl group or ether is preferred. Preferred examples thereof include structures consisting of amine and (thio)carbonyl group such as —NH—C(=S)—NH—, and —NH—(CH$_2$)$_{1-4}$—O—, but not restricted thereto.

Preferred examples of X''' in Formula [VI] include those represented by the following Formula [VII], such as well-known Rhodamine and fluorescein.

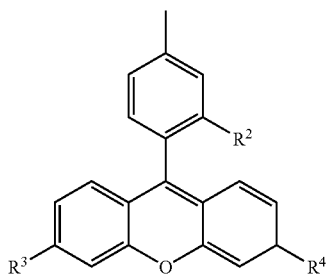

[VII]

(In Formula [VII], $R^2$ represents a hydrogen atom or carboxyl, $R^3$ and $R^4$ independently represent hydroxyl, $C_1$–$C_6$ alkyl, or dialkylamino in which each alkyl group has 1 to 6 carbon atoms (the nitrogen atom therein may form a double bond with a carbon atom constituting the ring to form a quaternary amine).

Among the structures represented by Formula [III], which have the fluorescent group represented by Formula [VII], especially preferred include those represented by the following Formula [VIII]:

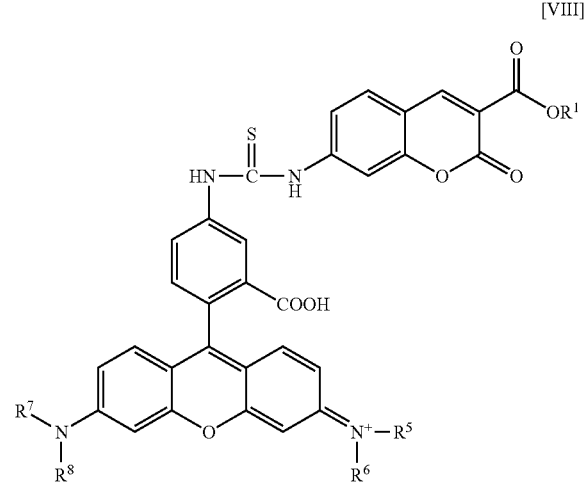

[VIII]

(wherein $R^1$ represents the same meaning as in said Formula [I]; and $R^5$, $R^6$, $R^7$ and $R^8$ independently represent $C_1$–$C_6$ alkyl).

As the preferred examples of the fluorescent probes represented by Formula [III], those having the structures represented by the following Formula [X], in which amine is bound to the coumarin derivative, are cited:

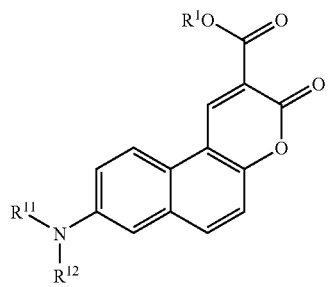
[X]

(wherein $R^1$ represents the same meaning as in Formula [I]; $R^{11}$ and $R^{12}$ independently represent hydrogen, hydroxyl, halogen, $C_1$–$C_6$ alkyl, $C_1$–$C_6$ haloalkyl, $C_1$–$C_6$ alkoxyl, $C_1$–$C_6$ haloalkoxyl, benzyl or acetyl, or a group containing one or two monosaccharide structures or an acylate thereof).

Among the compounds represented by Formula [X], those wherein the group containing one or two monosaccharide structures or an acylate thereof is glycosyl, glycoside, fructosyl, fructoside or a group represented by Formula [XI]:

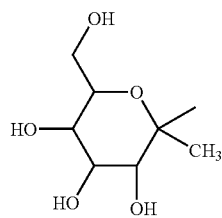
[XI]

with the proviso that 1 to 4 hydroxyl groups in these groups may be acylated with $C_1$–$C_6$ acyl group(s), are preferred.

Further, those wherein the monosaccharide structure is bound to the nitrogen atom in Formula [X] through $C_1$–$C_6$ alkyl or $C_1$–$C_6$ alkoxyl group are preferred.

Preferred examples of such compounds include those represented by the following Formula [XII]:

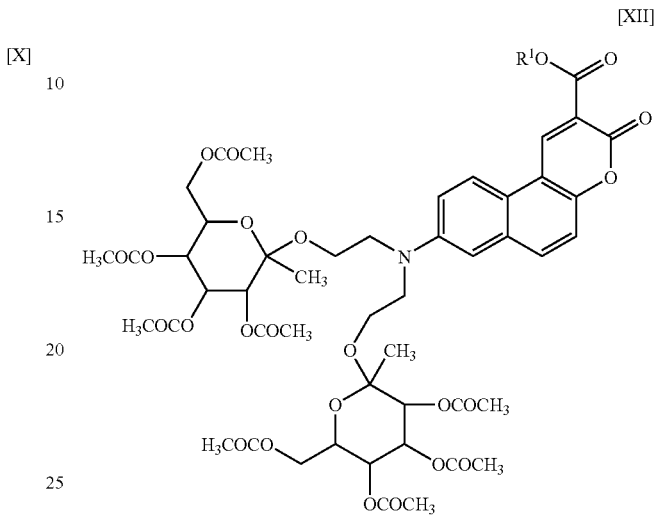
[XII]

In cases where X″ in the Formula [III] is represented by the above-described Formula [VI], $$X'''\text{-}Z\text{-} \quad [VI]$$

preferred examples of the groups represented by Formula [VI] include those represented by the following Formula [XVI]:

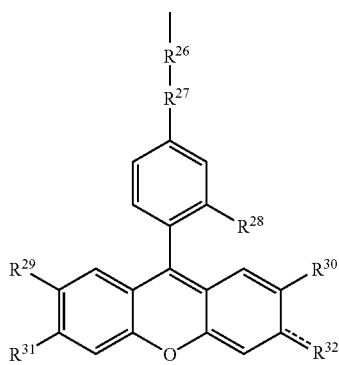
[XVI]

(wherein $R^{26}$ may or may not exist, when it exists, $R^{26}$ represents $C_1$–$C_5$ alkylene; $R^{27}$ represents —NH—, —NH—CO— or —OCO—; $R^{28}$ represents hydrogen, carboxyl or —COOR$^{33}$ (wherein $R^{33}$ represents a monovalent metal atom or $C_1$–$C_5$ alkyl); $R^{29}$ and $R^{30}$ independently represent hydrogen, $C_1$–$C_5$ alkyl or halogen; $R^{31}$ represents hydroxyl, $C_1$–$C_5$ alkyl or dialkylamino in which each alkyl group has 1 to 5 carbon atoms; the symbol "----" which binds $R^{32}$ and the ring represents single bond or double bond, in cases where it represents single bond, $R^{32}$ represents hydroxyl, $C_1$–$C_5$ alkyl, or dialkylamino in which each alkyl group has 1 to 5 carbon atoms; in cases where it represents double bond, $R^{32}$ represents carbonyl or =$N^+R^{34}R^{35}$ (wherein $R^{34}$ and $R^{35}$ independently represent $C_1$–$C_5$ alkyl).

In cases where $R^{27}$ is —NH—CO— or —OCO—, the direction (that is, in case of —NH—CO, whether the —NH— is above or below the —CO— in Formula [XVI], and in case of —OCO—, whether the —O— is above or below the —CO— in Formula [XVI]) is not restricted, and both are included.

Among the compounds represented by Formula [XVI], those wherein $R^{28}$ is hydrogen or carboxy, $R^{29}$ and $R^{30}$ are hydrogen, $R^{31}$ is dialkylamino, and $R^{32}$ is a dialkyl quaternary amine bound to the ring via double bond, are preferred, and especially those wherein $R^{26}$ is methylene, $R^{27}$ is —NH—, all of $R^{28}$, $R^{29}$ and $R^{30}$ are hydrogen atoms, $R^{31}$ is $N(CH_3)_2$, and $R^{32}$ is =$N^+(CH_3)_2$ are especially preferred.

Those represented by Formula [XVI] having Rhodamine or fluorescein, preferably Rhodamine, as the fluorescent chromophor, have high molar absorption coefficients and quantum yields, and good optical stabilities, and their fluorescent intensities do not depend on pH. Further, Rhodamine is now used as a stain for mitochondria in the cells. It has been proved that KMG-20 and its analogues are uniformly dispersed in the cytoplasm, especially in the area surrounding the nucleus. By using the compound represented by Formula [XVI], more topical area in the cells may be stained and the behavior of magnesium ions therein may be observed.

The fluorescent probes according to the present invention may be easily produced by known methods. In particular, since the preferred fluorescent probes according to the present invention may be obtained by binding a coumarin derivative having a carboxyl group or an ester or salt thereof with a known fluorescent group, synthesis of the fluorescent probes according to the present invention is easy for those skilled in the art.

The fluorescent probe according to the present invention may be used by exactly the same method as the conventional fluorescent probes, that is, by treating a sample with the fluorescent probe, and measuring fluorescence under irradiation with excitation light. For example, the fluorescent probe dissolved in a polar organic solvent such as dimethylsulfoxide (DMSO) is added to a buffer, and a sample is added thereto (or the probe solution is added to a sample). After incubation, excitation light is irradiated to the mixture and the fluorescent is measured. The concentration of the probe in the polar organic solvent is not restricted, and usually about 0.1 mM to 10 mM, preferably about 0.5 mM to 2 mM. The concentration of the probe after being added to the buffer is not restricted, and usually, about 1 μM to 0.1 mM, preferably about 5 μM to 20 μM. The time for the incubation is not restricted and may be appropriately selected depending on the sample. Usually, the incubation time may be about 5 minutes to 1 hour. The incubation temperature is not restricted, and a temperature suited for the respective sample may be selected, and usually about 0° C. to 40° C. In cases where the sample is cells or a tissue, the temperature suited for culturing the cells or tissue (for example, in case of human cells or tissue, 37° C.) is preferred. Measurement of fluorescence may be carried out by using a commercially available fluorometer. In case of investigation of behavior of magnesium ions in cells, fluorescence may be observed by using a fluorescence microscope or a confocal laser microscope. These measuring methods per se are known. The sample is not restricted, and any sample containing magnesium ions which are desired to be observed may be employed. Preferred examples of the sample include various cells and tissues. In cases where the sample is cells or a tissue, the culture medium for the cells or the tissue is replaced with the above-described fluorescent probe solution, and the fluorescence is measured after the incubation as mentioned above.

EXAMPLES

The present invention will now be described by way of examples thereof. However, the present invention is not restricted to the following examples.

Example 1

Production of Fluorescent Probe (13-aza-3-oxa-4-oxotetracyclo[7.7.1.0<2,7>.0<13,17>]heptadeca-1(17),2(7),5,8-tetraene-5-ylcarbonyloxy)methyl acetate (KMG-20)

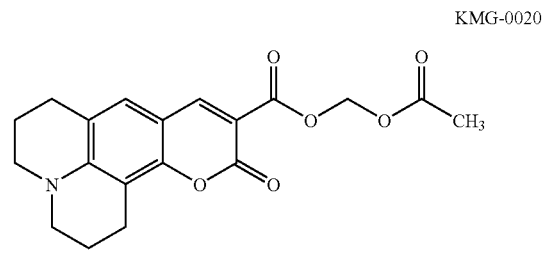

(1) Synthesis of 9-azatricyclo[7.3.1.0<5,13>]trideca-1(13),2,4-triene-2-ol

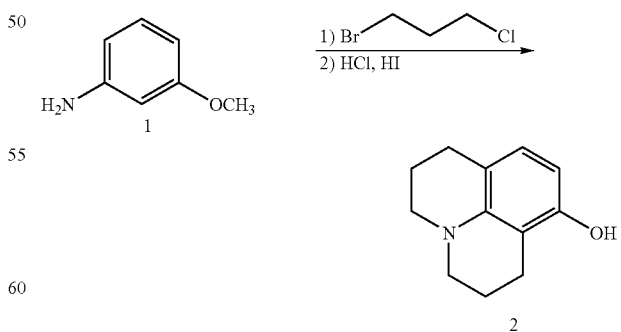

To a 100 ml two-necked flask, 1.0 g (8.13 mmol) of 3-methoxyaniline and 5.0 ml of 1-bromo-3-chloropropane were added, and the resulting mixture was stirred under nitrogen at 70° C. for 1 hour and then at 100° C. for 2 hours, followed by heating the mixture to reflux for 11 hours. After allowing the mixture to cool, conc. hydrochloric acid and water were slowly added. After extraction with ether, the organic layer was dried over anhydrous magnesium sulfate. The solvent was evaporated under reduced pressure and the obtained residue was purified by column chromatography to obtain the desired compound.

(2) Synthesis of 9-aza-2-hydroxytricyclo[7.3.1.0<5,13>]trideca-1(13),2,4-triene-3-carbaldehyde

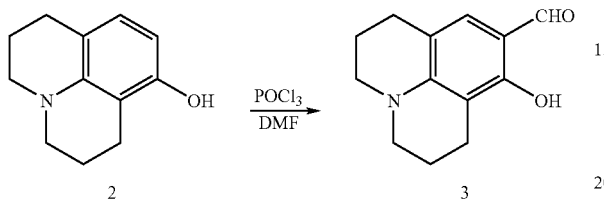

To a 10 ml two-necked flask, 1.0 g (5.29 mol) of Compound 2 was added, and 5.0 ml of dry DMF was added after replacing the atmosphere with nitrogen. In 5 ml of dry DMF, 0.65 ml (6.42 mmol) of POCl$_3$ was dissolved, and the obtained solution was slowly added dropwise. The resulting mixture was stirred at room temperature for 30 minutes, and then water was added to stop the reaction. The obtained precipitates were recovered and recrystallized from hexane to obtain the desired compound.

(3) Synthesis of methyl 13-aza-3-oxa-4-oxotetracyclo[7.7.1.0<2,7>.0<13,17>]heptadeca-1(17),2(7),5,8-tetraene-5-carboxylate

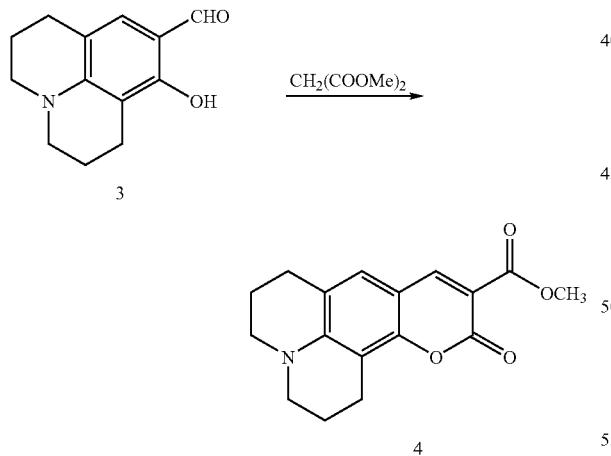

To a 100 ml two-necked flask, 1.0 g (4.61 mmol) of Compound 3, 0.6 ml (5.50 mmol) of methyl malonate, 0.7 g (7.48 mmol) of piperidine, 10.0 ml of acetonitrile and 20.0 ml of benzene were added, and the obtained mixture was heated to reflux for 3 hours. After evaporation of the solvent under reduced pressure, water was added and the mixture was extracted with ether. The organic layer was dried over anhydrous sodium sulfate, and the residue was purified by column chromatography to obtain the desired compound.

(4) Synthesis of 13-aza-3-oxa-4-oxotetracyclo[7.7.1.0<2,7>.0<13,17>]heptadeca-1(17),2(7),8-triene-5-carboxylic acid

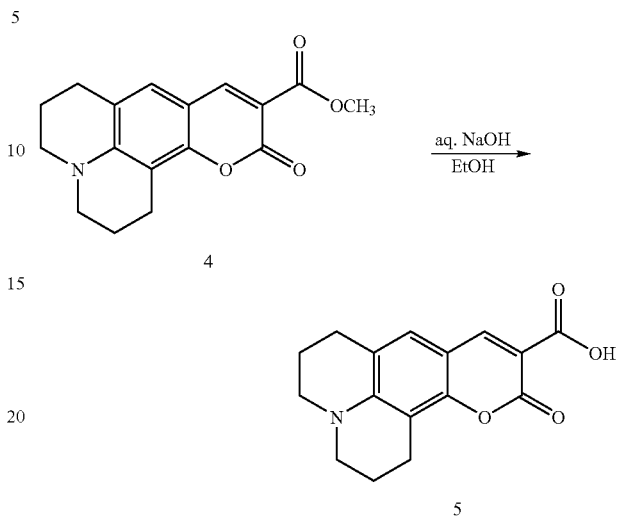

To a 100 ml eggplant type flask, 1.0 g (3.48 mmol) of Compound 4, 5.0 ml of 5% aqueous sodium hydroxide solution, and 50.0 ml of ethanol were added, and the obtained mixture was heated to reflux for 12 hours. After allowing the mixture to cool, 1.0N hydrochloric acid was added to make the mixture acidic, and the mixture was extracted with ether. The organic layer was washed with water and then dried over anhydrous sodium sulfate. The solvent was evaporated under reduced pressure and the residue was then dried under reduced pressure by a pump.

From the thus obtained coumarin 343, (13-aza-3-oxa-4-oxotetracyclo[7.7.1.0<2,7>.0<13,17>]heptadeca-1(17),2(7),5,8-tetraene-5-ylcarbonyloxy)methyl acetate (KMG-20) was synthesized according to the following equation:

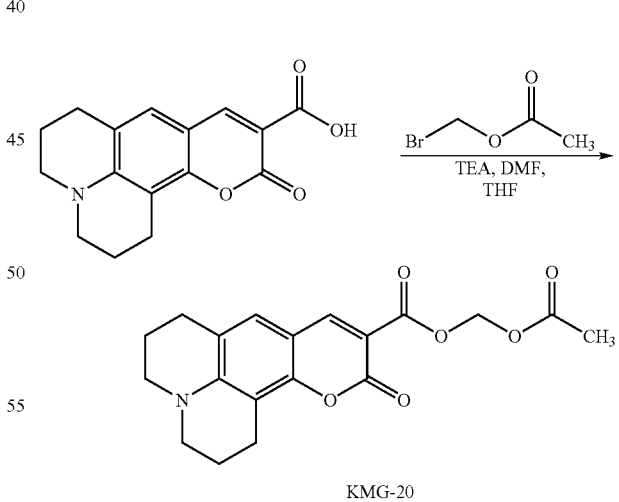

KMG-20

That is, to a 50 ml two-necked flask, 0.10 g (0.35 mmol) of coumarin 343 obtained as described above was added, and the atmosphere was changed to nitrogen after degassing. Then 10.0 ml of dimethylformamide (DMF), 10.0 ml of tetrahydrofuran (THF) and 0.07 g (0.70 mmol) of triethylamine (TEA) were added, and the obtained mixture was stirred at room temperature for 1 hour. To the mixture, 0.10 g (0.70 mmol) of acetoxymethyl bromide was added, and the mixture was stirred at room temperature for 12 hours. After evaporation of the solvent under reduced pressure, the residue was washed once with 50 ml of 0.1N hydrochloric acid, and then three times with 50 ml of saturated saline, and then dried over anhydrous sodium sulfate. After evaporation of the solvent under reduced pressure, the residue was purified by column chromatography (SiO$_2$; CHCl$_3$:MeOH=20:1) to obtain a yellow solid. Identification was carried out using $^1$H-NMR, ESI-TOF mass analysis.

Yield 52%

$^1$H-NMR (300 MHz, CDCl$_{13}$, TMS, r.t., δ/ppm) 1.90–2.05 (m, 4H), 2.13 (s, 3H), 2.77 (t, 2H), 2.88 (t, 2H), 3.36 (q, 4H), 5.94 (s, 2H), 6.93 (s, 1H), 8.35 (s, 1H) ESI-TOF [M+Na]$^+$=380

Example 2

Synthesis of Fluorescent Probe ((17-aza-5-oxa-6-oxopentacyclo[11.7.1.0<2,11>.0<4,9>.0<17,21>] henicosa-1(21),2(11),3,7,9(10),12-hexaene-7-ylcarbonyloxy)methyl acetate)

According to the following reaction equation, (17-aza-5-oxa-6-oxopentacyclo[11.7.1.0<2,11>.0<4,9>.0<17,21>] henicosa-1(21),2(11), 3,7,9(10),12-hexaene-7-ylcarbonyloxy)methyl acetate (Compound 6) was synthesized.

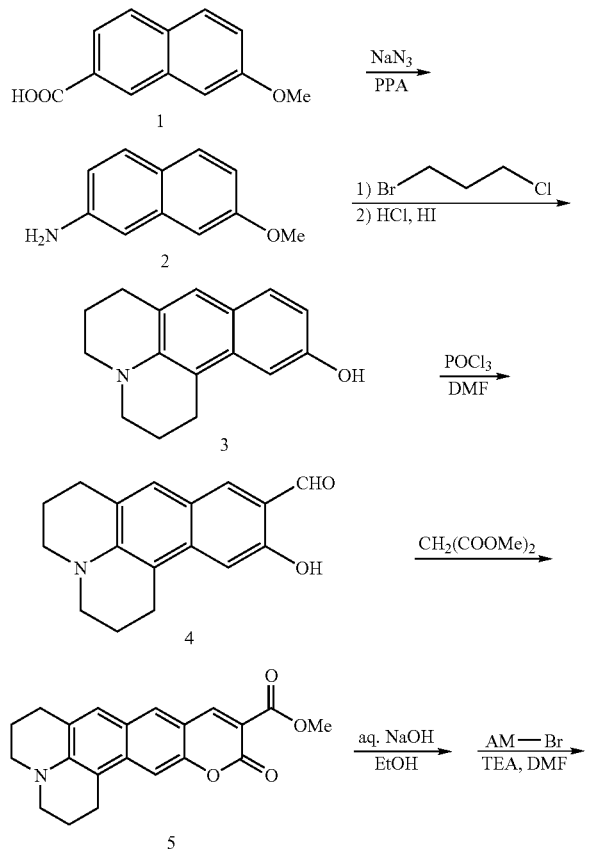

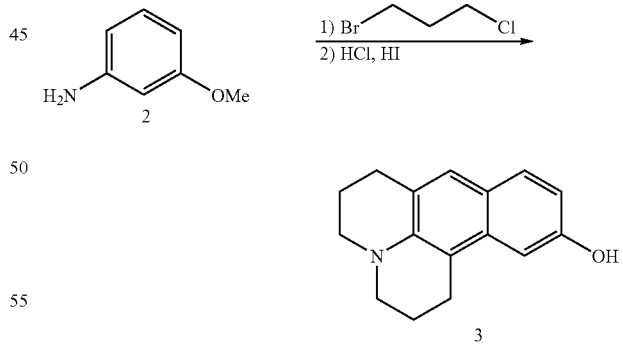

(1) Synthesis of 6-methoxy-2-naphthylamine

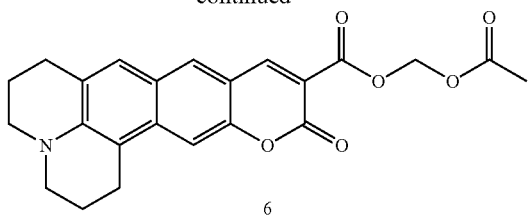

To a 50 ml two-necked flask, 1.0 g (3.5 mmol) of 6-methoxynaphthalene-2-carboxylic acid (Compound 1), 2.28 g (35.0 mmol) of sodium azide and 15.0 g of polyphosphoric acid (PPA) were added, and the mixture was stirred at 40° C. for 12 hours. To the resulting mixture, 100 g of ethyl acetate was added and the obtained mixture was washed with saturated aqueous sodium hydrogen carbonate, followed by drying the product over anhydrous sodium sulfate. The solvent was evaporated under reduced pressure and the residue was purified by silica gel column chromatography to obtain the desired compound.

(2) Synthesis of 13-aza-4-hydroxytetracyclo[7.7.1.0<2,7>.0<13,17>]heptadeca-1(17),2(7),3,5,8-pentaene-4-ol

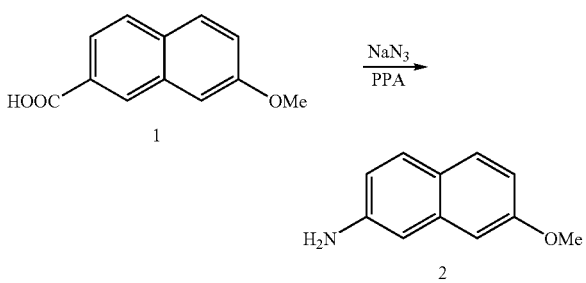

To a 100 ml two-necked flask, 1.0 g (5.78 mmol) of Compound 2 and 1.0 g of 1-bromo-3-chloropropane were added, and the resulting mixture was stirred under nitrogen at 70° C. for 1 hour and then at 100° C. for 2 hours, followed by heating the mixture to reflux for 11 hours. After allowing the mixture to cool, conc. hydrochloric acid and water were slowly added. After extraction with ether, the organic layer was dried over anhydrous magnesium sulfate. The solvent was evaporated under reduced pressure and the obtained residue was purified by column chromatography to obtain the desired compound.

(3) Synthesis of 13-aza-4-hydroxytetracyclo[7.7.1.0<2,7>.0<13,17>]heptadeca-1(17),2(7),3,5,8-pentaene-5-carbaldehyde

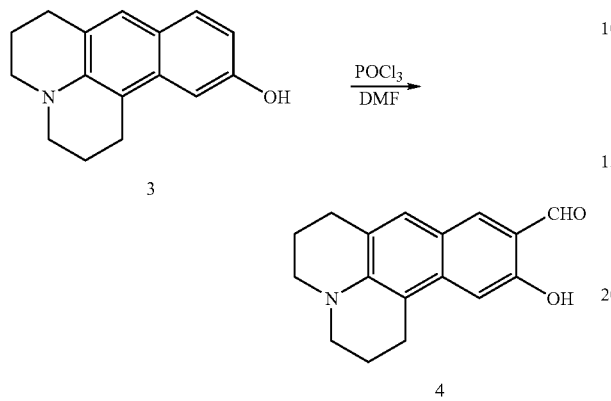

To a 10 ml two-necked flask, 1.0 g (4.18 mol) of Compound 3 was added, and 5.0 ml of dry DMF was added after replacing the atmosphere with nitrogen. In 5 ml of dry DMF, 0.65 ml (6.42 mmol) of POCl$_3$ was dissolved, and the obtained solution was slowly added dropwise. The resulting mixture was stirred at room temperature for 30 minutes, and then water was added to stop the reaction. The obtained precipitates were recovered and recrystallized from hexane to obtain the desired compound.

(4) Synthesis of methyl 17-aza-5-oxa-6-oxopentacyclo[11.7.1.0<2,11>.0<4,9>.0<17,21>]henicosa-1(21),2(11),3,7,9(10),12-hexaene-7-carboxylate

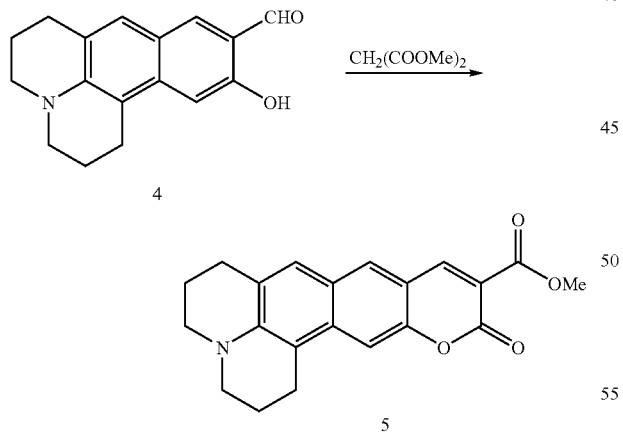

To a 100 ml two-necked flask, 1.0 g (3.74 mmol) of Compound 4, 0.6 ml (5.50 mmol) of methyl malonate, 0.7 g (7.48 mmol) of piperidine, 10.0 ml of acetonitrile and 20.0 ml of benzene were added, and the obtained mixture was heated to reflux for 3 hours. After evaporation of the solvent under reduced pressure, water was added and the mixture was extracted with ether. The organic layer was dried over anhydrous sodium sulfate, and the residue was purified by column chromatography to obtain the desired compound.

(5) Synthesis of (17-aza-5-oxa-6-oxopentacyclo[11.7.1.0<2,11>.0<4,9>.0<17,21>]henicosa-1(21),2(11), (11),3,7,9(10),12-hexaene-7-ylcarbonyloxy)methyl acetate

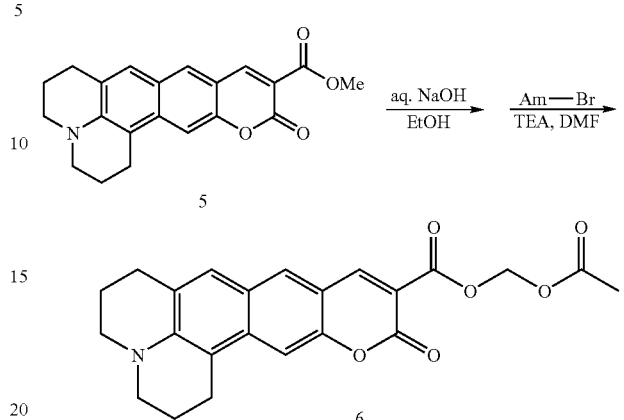

To a 100 ml eggplant type flask, 1.0 g (2.86 mmol) of Compound 5, 5.0 ml of 5% aqueous sodium hydroxide solution, and 50.0 ml of ethanol were added, and the obtained mixture was heated to reflux for 12 hours. After allowing the mixture to cool, 1.0N hydrochloric acid was added to make the mixture acidic, and the mixture was extracted with ether. The organic layer was washed with water and then dried over anhydrous sodium sulfate. The solvent was evaporated under reduced pressure and the residue was then dried under reduced pressure by a pump.

To the obtained compound, 10.0 ml of DMF and 0.29 ml (2.86 mmol) of triethylamine were added, and the obtained mixture was placed in an ice bath under nitrogen gas flow. To the mixture, acetoxymethyl bromide (4.29 mmol) was added, and the resulting mixture was stirred in the ice bath for 30 minutes and then at room temperature for 12 hours. After evaporation of the solvent under reduced pressure, methylene chloride was added to the obtained compound, and the resulting mixture was washed with 0.1N hydrochloric acid and then with saturated saline. The resultant was dried over anhydrous magnesium sulfate, and the solvent was evaporated under reduced pressure. The residue was purified by column chromatography to obtain the desired product.

Example 3

Synthesis of Fluorescent Probe (5-((((3-((acetyloxymethyl)oxycarbonyl)-2-oxo (2H-cromene-7-yl))amino)thioxomethyl)amino)-2-(6-(diethylamino)-3-(diethylidene)xanthene-9-yl)benzoic acid)

In accordance with the following reaction equation, 5-((((3-((acetyloxymethyl)oxycarbonyl)-2-oxo (2H-cromene-7-yl))amino)thioxomethyl)amino)-2-(6-(diethylamino)-3-(diethylidene)xanthene-9-yl)benzoic acid) (Compound 5) was synthesized.

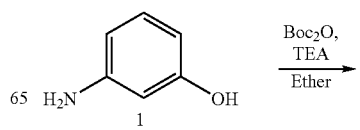

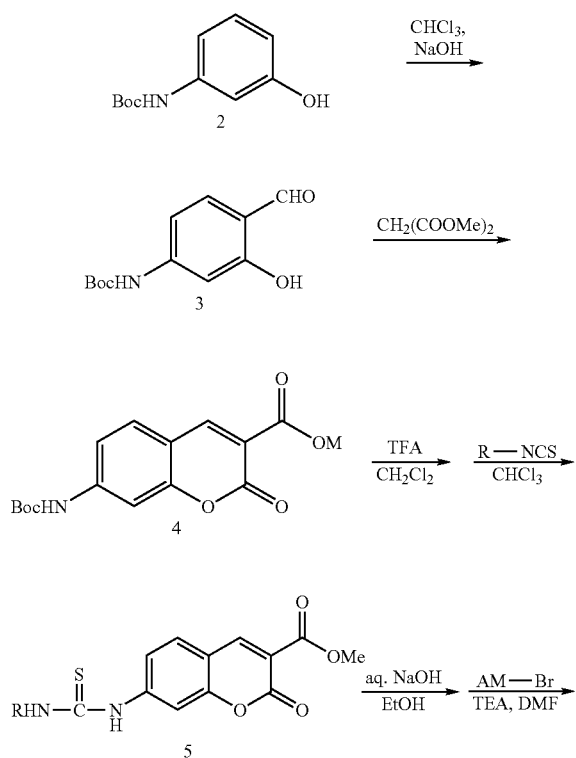

(1) Synthesis of (tert-butoxy)-N-(3-hydroxyphenyl)formamide

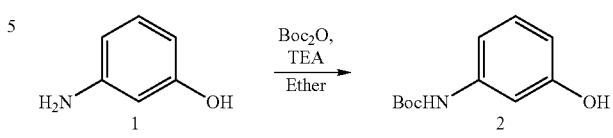

To a 100 ml two-necked flask, 1.0 g (9.17 mmol) of 3-aminophenol (Compound 3) was added and the atmosphere was replaced with nitrogen. Then 50 ml of diethyl ether and 0.92 ml (9.17 mmol) of triethylamine were added and the flask was immersed in an ice bath. To the mixture, 1.99 g (9.17 mmol) of di-tert-butyldicarbonate was added and the mixture was stirred for 2 hours at room temperature. The solvent was evaporated under reduced pressure, and the residue was purified by column chromatography ($SiO_2$, ethyl acetate:n-hexane=1:1) to obtain the desired compound.

(2) Synthesis of (tert-butoxy)-N-(4-formyl-3-hydroxyphenyl)formamide

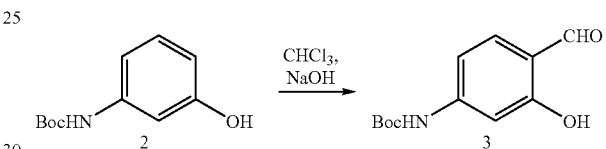

To a 50 ml eggplant type flask, 1.0 g (4.78 mmol) of Compound 2, 10.0 ml of chloroform and 10.0 ml of 5% aqueous NaOH solution were added, and the mixture was stirred at 60° C. for 2 hours. After evaporation of the most part of the solvent, the residue was extracted with ether, and the organic layer was dried over anhydrous magnesium sulfate. The solvent was evaporated under reduced pressure to obtain the desired product.

(3) Synthesis of methyl 7-((tert-butoxy)carbonylamino)-2-oxo-2H-cromene-3-carboxylate

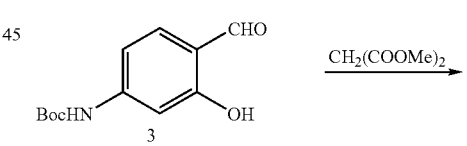

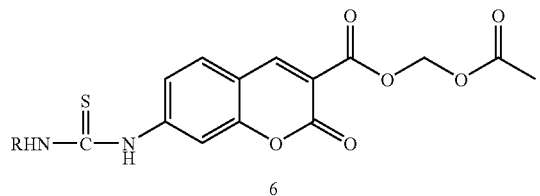

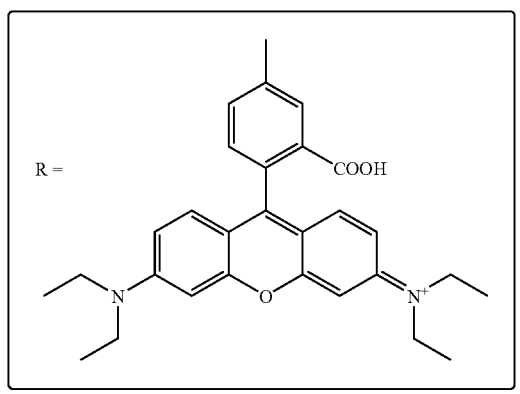

To a 100 ml eggplant type flask, 1.0 g (4.22 mmol) of Compound 3, 30 ml of benzene, 20 ml of acetonitrile, 0.83 g (6.33 mmol) of methyl malonate and 1.08 g (12.65 mmol) of piperidine were added, and the mixture was heated to reflux for 3 hours. After evaporation of the solvent, water was added, and the resulting mixture was extracted with benzene. The organic layer was dried over anhydrous sod sulfate, and the solvent was evaporated under reduced pressure. The residue was chromatography to obtain the desired product.

(4) Synthesis of 2-(6-(diethylamino)-3-(diethylidene)xanthene-9-yl)-5-((((3-(methoxycarbonyl)2-oxo (2H-cromene-7-yl))amino)thioxomethyl)amino)benzoic acid (5) Synthesis of 5-((((3-((acetyloxymethyl)oxycarbonyl)-2-oxo (2H-cromene-7-yl))amino)thioxomethyl)amino)-2-(6-(diethylamino)-3-(diethylidene)xanthene-9-yl)benzoic acid

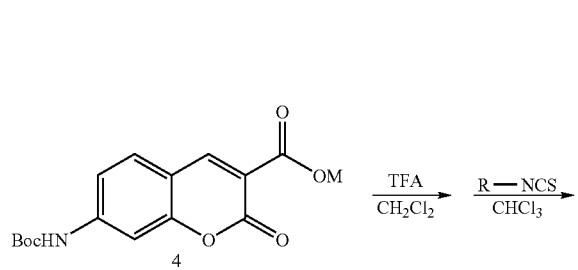

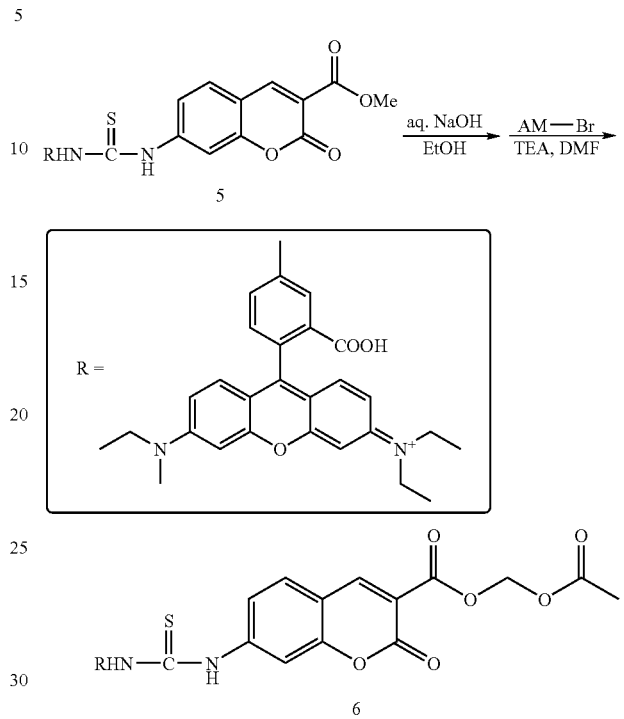

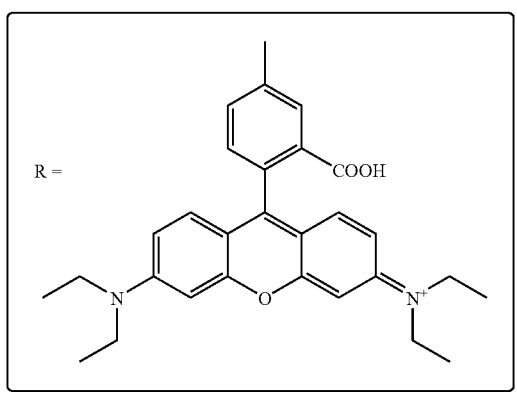

To a 50 ml two-necked flask, 1.0 g (3.13 mmol) of Compound 4, 20.0 ml of methylene chloride and 5.0 ml of trifluoroacetic acid were added, and the mixture was stirred for 1 hour at room temperature. The solvent was evaporated under reduced pressure and the residue was then dried under reduced pressure by a pump.

To the obtained compound, 10.0 ml of chloroform and 1.67 g (3.13 mmol) of Rhodamine isothiocyanate were added and the mixture was heated to reflux for 1 hour. The solvent was evaporated under reduced pressure and the residue was purified by column chromatography to obtain the desired product.

To a 100 ml eggplant type flask, 1.0 g (1.27 mmol) of Compound 5, 5.0 ml of aqueous 5% sodium hydroxide solution and 40 ml of ethanol were added, and the mixture was heated to reflux for 10 hours. After allowing the mixture to cool, most part of the solvent was evaporated under reduced pressure, and 1N hydrochloric acid was added to make the mixture acidic.

To the obtained compound, 40 ml of DMF and 0.28 ml (2.80 mmol) of triethylamine were added, and the mixture was cooled in an ice bath. To the mixture, 0.40 ml (2.80 mmol) of acetoxymethyl bromide was added, and the resulting mixture was stirred in an ice bath for 30 minutes and then at room temperature for 24 hours. The solvent was evaporated under reduced pressure and the residue was reprecipitated in acetone-methylene chloride to obtain the desired product.

Example 4

Synthesis of Fluorescent Probe (methyl-13-aza-10,10,16,16-tetramethyl-3-oxa-4-oxo-tetracyclo[7,7,1,0<2,7>.O<13,17>]heptadeca-1(17),2(7),5,8-tetraene-5-carboxylate)(KMG-27)

In accordance with the reaction scheme below, methyl-13-aza-10,10,16,16-tetramethyl-3-oxa-4-oxo-tetracyclo[7,7,1,0<2,7>.O<13,17>]heptadeca-1(17),2(7),5,8-tetraene-5-carboxylate (4) was synthesized.

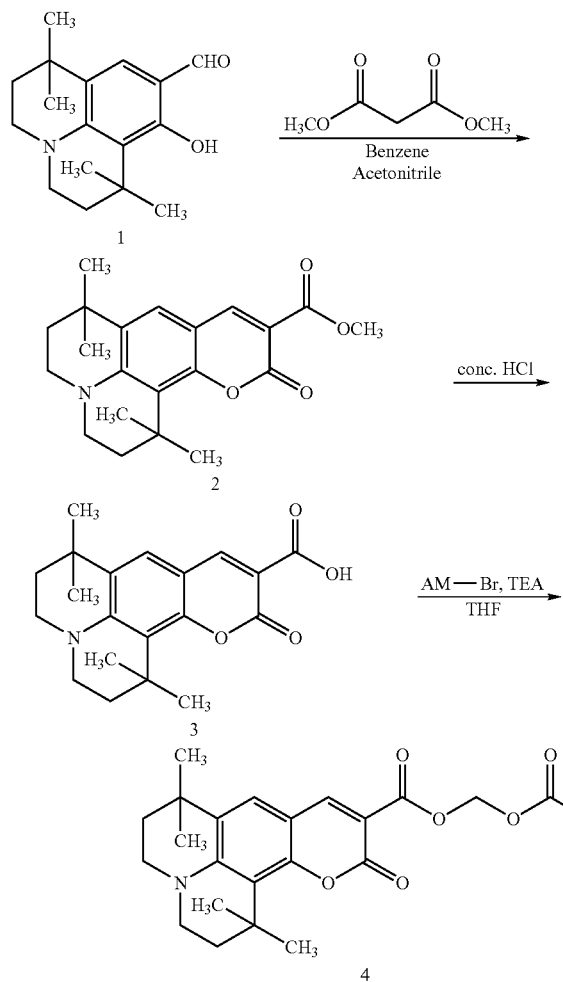

(1) Synthesis of methyl-13-aza-10,10,16,16-tetramethyl-3-oxa-4-oxotetracyclo[7.7.1.0<2,7>.O<13,17>]hepta-1(17),2(7),5,8-tetraene-5-carboxylate

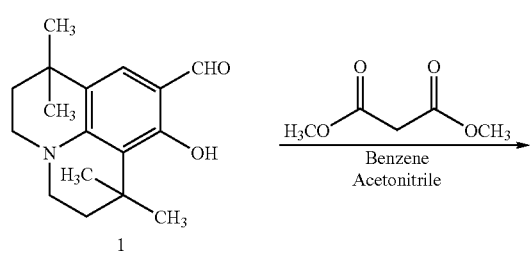

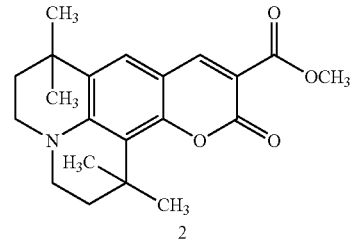

To a 100 ml eggplant type flask, 0.70 g (2.56 mmol) of 8-hydroxy-1,1,7,7-tetramethyljulolidine-9-carboxyaldehyde (1) and 0.51 g (3.84 mmol) of dimethyl malonate, 35.0 ml of benzene and 15.0 ml of acetonitrile were added, and the mixture was heated to reflux for 4 hours under nitrogen gas flow. After evaporation of the solvent, the residue was dissolved in ethyl acetate, and washed with saturated saline.

The organic layer was dried over anhydrous sodium sulfate and the solvent was evaporated under reduced pressure. The residue was purified by column chromatography (SiO2,CH$_2$Cl$_2$→CH$_2$Cl$_2$:AcOEt=1:1v/v) to obtain yellow solid.

Yield: 78%

$^1$H NMR (300 MHz, CDCl$_3$, r.t., TMS, δ/ppm) 1.29 (s, 6H), 1.54 (s, 6H), 1.72~1.81 (m, 4H), 3.28 (t, 2H), 3.38 (t, 2H), 3.89 (s, 3H), 7.15 (s, 1H), 8.37(s, 1H).

ESI-TOFMS (+): 378.18 [M+Na]$^{30}$

Elementary Analysis: C$_{21}$H$_{25}$NO$_4$:

Calcd.: C, 70.96; H, 7.09; N, 3.94.

Found: C, 71.03; H, 7.12; N, 4.01.

(2) Synthesis of 13-aza-10,10,16,16-tetramethyl-3-oxa-4-oxotetracyclo[7.7.1.0<2,7>.0<13,17>]heptadeca-1(17),2(7),5,8-tetraene-5-carboxylic acid (3)

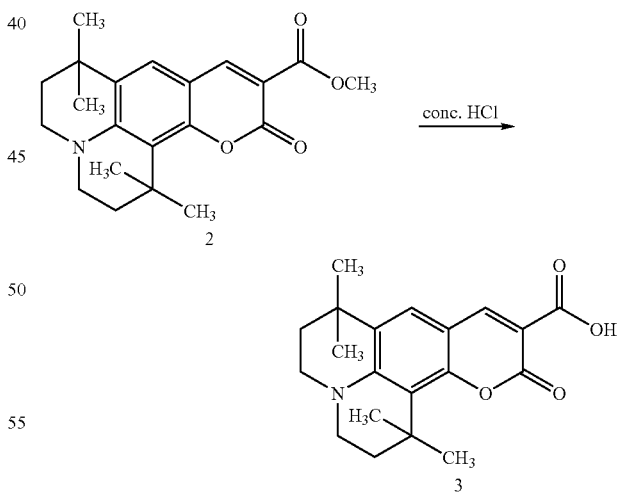

To a 100 ml eggplant type flask, Compound 2 and 5.0 ml of conc. hydrochloric acid were added, and the mixture was stirred at room temperature for 24 hours. The reaction solution was poured into iced water, and then extracted with methylene chloride. The organic layer was washed with water and dried over anhydrous sodium sulfate. The solvent was evaporated under reduced pressure to obtain an orange solid.

Yield: 95%

¹H NMR (300 MHz, CDCl₃, r.t., TMS, δ/ppm) 1.30 (s, 6H), 1.55 (s, 6H), 1.74–1.85 (m, 4H), 3.36 (t, 2H), 3.44 (t, 2H), 3.89 (s, 3H), 7.23 (s, 1H), 8.55(s, 1H).

ESI-TOFMS (+): 364.16 [M+Na]⁺

Elementary Analysis: $C_{20}H_{23}NO_4$:

Calcd.: C, 70.36; H, 6.79; N, 4.10.

Found: C, 70.54; H, 6.90; N, 4.15.

(3) Synthesis of methyl-13-aza-10,10,16,16-tetramethyl-3-oxa-4-oxo-tetracyclo[7,7,1,0<2,7>.O<13,17>]heptadeca-1(17),2(7),5,8-tetraene-5-carboxylate (4)

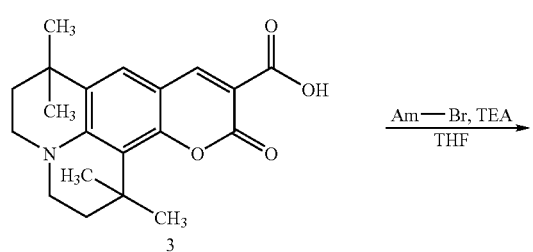

Under nitrogen gas flow, 0.10 g (0.29 mmol) of Compound 3, 0.04 g (0.35 mmol) of triethylamine and 5.0 ml of dry THF were added to a 30 ml two-necked flask, and the flask was immersed in an ice bath. To the mixture, 0.05 g (0.35 mmol) of bromomethyl acetate (AM-Br) was added, and the resulting mixture was stirred at room temperature for 24 hours. After evaporation of the solvent under reduced pressure, the reaction mixture was dissolved in methylene chloride and washed with water. The organic layer was dried over anhydrous sodium sulfate, and the solvent was evaporated under reduced pressure. The residue was purified by large thin layer chromatography (SiO₂, n-hexane:ethyl acetate=10:7 v/v) to obtain an orange solid.

Yield : 75%.

¹H NMR (300 MHz, CDCl₃, r.t., TMS, δ/ppm) 1.30 (s, 6H), 1.55 (s, 6H), 1.72–1.85 (m, 4H), 2.12 (s, 3H), 3.36 (t, 2H), 3.44 (t, 2H), 3.89 (s, 3H), 5.95 (s, 2H) 1H), 8.38(s, 1H).

ESI-TOFMS (+): 436.15 [M+Na]⁺

Elementary Analysis: $C_{23}H_{27}NO_6$:

Calcd.: C, 66.81; H, 6.58; N, 3.39.

Found: C, 66.97; H, 6.51; N, 3.24.

Example 5

Synthesis of (13-aza-10,16-dihydroxy-3-oxa-4-oxotetracyclo[7.7.1.0<2,7>.0<13,17>]heptadeca-1(17),2(7),5,8-tetraene-5-ylcarbonyloxy)methyl acetate (7)

In accordance with the following reaction scheme, (13-aza-10,16-dihydroxy-3-oxa-4-oxotetracyclo[7.7.1.0<2,7>.0<13,17>]heptadeca-1(17),2(7),5,8-tetraene-5-ylcarbonyloxy)methyl acetate (7) was synthesized.

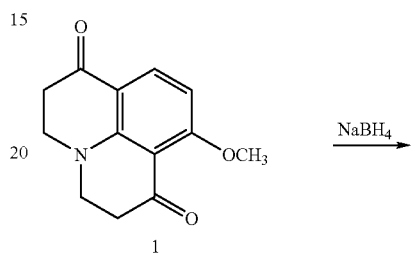

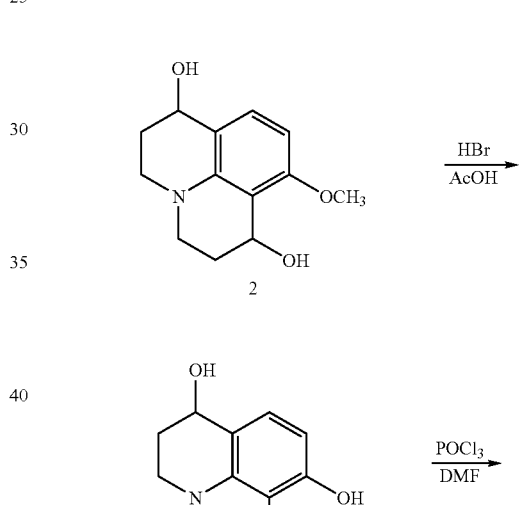

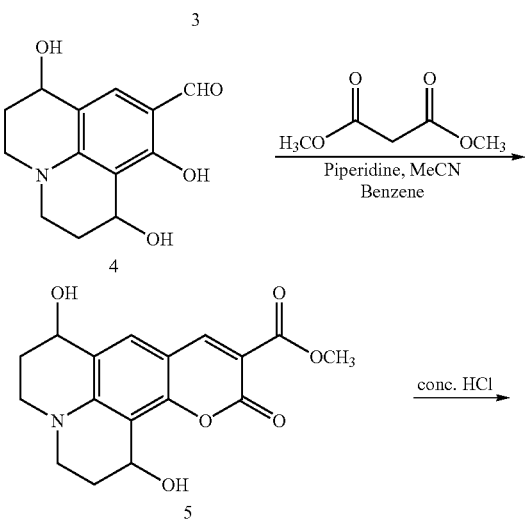

-continued

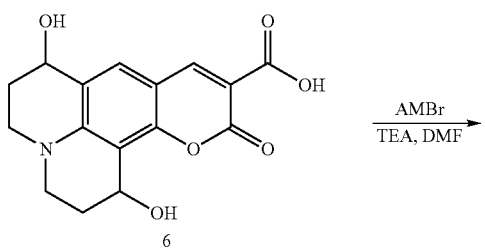

(2) Synthesis of 9-azatricyclo[7.3.1.0<5,13>trideca-1(13),2,4-triene-2,6,12-triol (3)

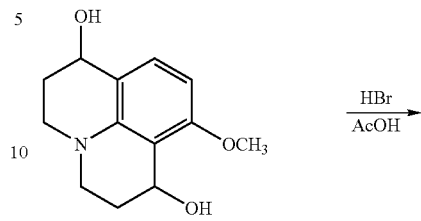

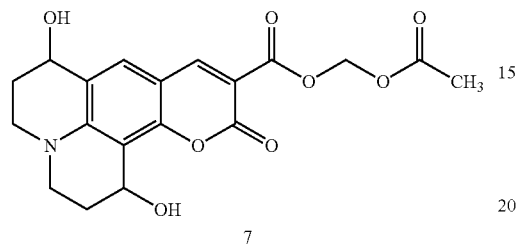

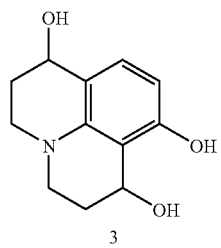

(1) Synthesis of 7-methoxy-2,3,4,5,3a-pentahydro-3a-azaphenalene-1,6-diol (2)

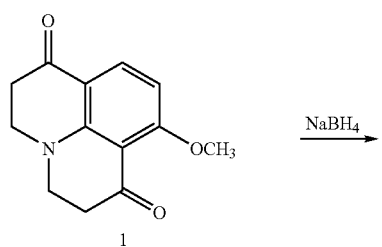

To a 50 ml eggplant type flask, 2.0 g (8.51 mmol) of Compound 2, 2.0 ml of hydrobromic acid and 10.0 ml of acetic acid were added, and the mixture was heated to reflux for 24 hours. The reaction solution was poured into cold water and then extracted with methylene chloride. The organic layer was washed with water and then dried over anhydrous sodium sulfate. After evaporation of the solvent, the residue was purified by column chromatography ($SiO_2$, $CH_2Cl_2$:ethyl acetate=3:1 v/v) to obtain the desired compound.

(3) Synthesis of 9-aza-2,6,12-trihydroxytricyclo[7.3.1.0<5,13>]trideca-1(13),2,4-triene-3-carboaldehyde (4)

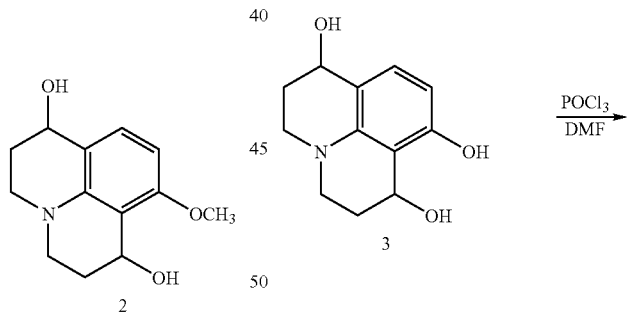

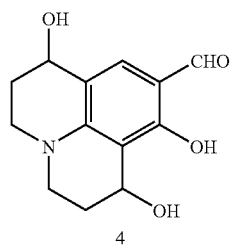

To a 50 ml eggplant type flask, 3.0 g (12.98 mmol) of 7-methoxy-2,3,4,5,3a-pentahydro-3a-azaphenalene-1,6-dione (1), 0.48 g (12.98 mmol) of sodium borohydride and 20 ml of ethanol were added, and the mixture was stirred at room temperature for 6 hours. After evaporation of the solvent under reduced pressure, the reaction mixture was dissolved in ethyl acetate, and washed with water. The organic layer was dried over anhydrous sodium sulfate and the solvent was evaporated under reduced pressure. The residue was purified by column chromatography ($SiO_2$, $CH_2Cl_2$) to obtain the desired product.

To a 50 ml three-necked flask, 1.0 g (4.52 mmol) of Compound 3, 20.0 ml of dry DMF and 0.69 g (4.52 mmol) of $POCl_3$ were added, and the mixture was stirred at room temperature for 12 hours under nitrogen gas flow. After evaporation of the solvent under reduced pressure, the reaction mixture was dissolved in methylene chloride and then washed with saturated saline. The organic layer was dried over anhydrous sodium sulfate and then purified by column chromatography (SiO$_2$, CH$_2$Cl$_2$:ethyl acetate=5:1 v/v) to obtain the desired compound.

(4) Synthesis of methyl-13-aza-10,16-dihydroxy-3-oxa-4-oxotetracyclo[7.7.1.0<2,7>.0<13,17>]heptadeca-1(17),2(7),5,8-tetraene-5-carboxylate (5)

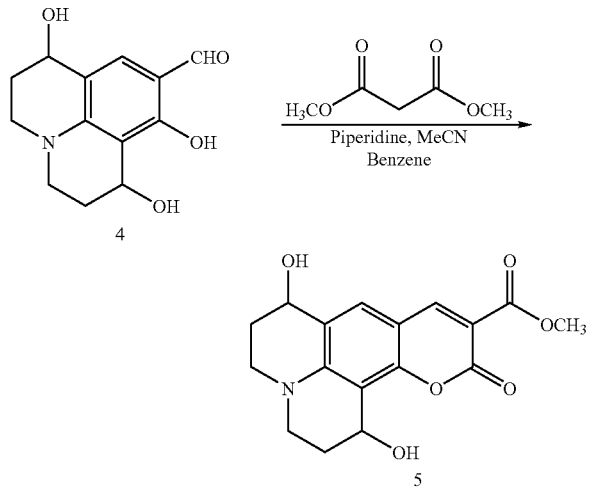

To a 100 ml eggplant type flask, 1.0 g (4.01 mmol) of Compound 4, 0.53 g (4.01 mmol) of dimethyl malonate, 35.0 ml of benzene, 15.0 ml of acetonitrile and 0.34 g (4.01 mmol) of piperidine were added, and the mixture was heated to reflux for 4 hours under nitrogen gas flow. After evaporation of the solvent under reduced pressure, the reaction mixture was dissolved in methylene chloride and washed with water. The organic layer was dried over anhydrous sodium sulfate and the solvent was evaporated under reduced pressure. The residue was purified by column chromatography (SiO$_2$, CH$_2$Cl$_2$:ethyl acetate=2:1 v/v) to obtain the desired compound.

(5) Synthesis of 13-aza-10,16-dihydroxy-3-oxa-4-oxotetracyclo[7.7.1.0<2,7>.0<13,17>]heptadeca-1(17),2(7),5,8-tetraene-5-carboxylic acid (6)

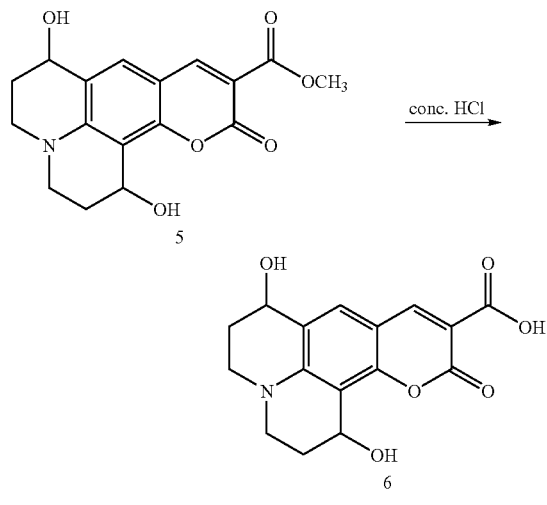

To a 50 ml eggplant type flask, 1.0 g (3.02 mmol) of Compound 5 and 10.0 ml of conc. hydrochloric acid were added, and the mixture was stirred at room temperature for 24 hours. The reaction solution was poured into cold water and then extracted with methylene chloride. The organic layer was washed with water and dried over anhydrous sodium sulfate. The solvent was evaporated under reduced pressure and the residue was purified by column chromatography (SiO$_2$, CH$_2$Cl$_2$) to obtain the desired product.

(6) Synthesis of (13-aza-10,16-dihydroxy-3-oxa-4-oxotetracyclo[7.7.1.0<2,7>.0<13,17>]heptadeca-1(17),2(7),5,8-tetraene-5-ylcarbonyloxy)methyl acetate (7)

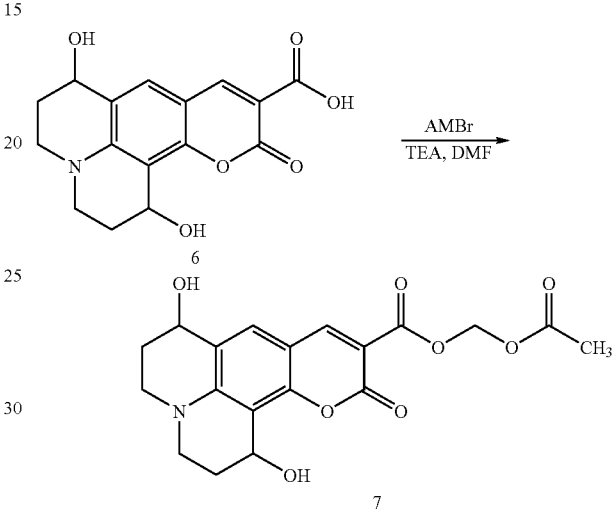

To a 50 ml two-necked flask, 0.50 g (1.58 mmol) of Compound 6, 20 ml of dry THF and 0.16 g (1.58 mmol) of triethylamine were added, and the flask was immersed in an ice bath. To the mixture, 0.29 g (1.58 mmol) of acetoxymethyl bromide was added, and the resulting mixture was stirred in the ice bath for 30 minutes and then at room temperature for 24 hours. After evaporation of the solvent under reduced pressure, the reaction mixture was dissolved in methylene chloride and washed with water. The organic layer was dried over anhydrous sodium sulfate, and the solvent was evaporated under reduced pressure. The residue was purified by large thin layer chromatography (SiO$_2$, CH$_2$Cl$_2$) to obtain the desired compound.

Example 6

Synthesis of 5-ethyl-6,6,8-trimethyl-3-oxo-4,5,6-trihydro-5-aza-4-oxanthracene-2-carboxylic acid (7)

In accordance with the following reaction scheme, 5-ethyl-6,6,8-trimethyl-3-oxo-4,5,6-trihydro-5-aza-4-oxanthracene-2-carboxylic acid (7) was synthesized.

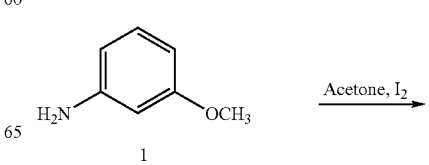

-continued

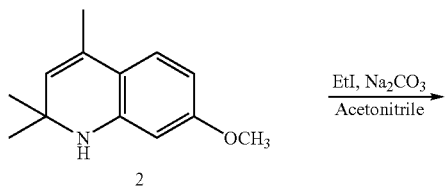
2

EtI, Na₂CO₃
———————→
Acetonitrile

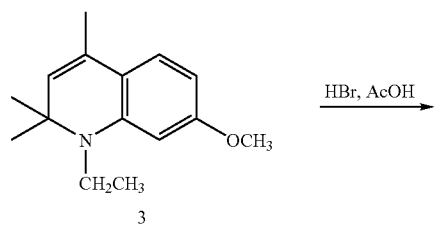
3

HBr, AcOH
———————→

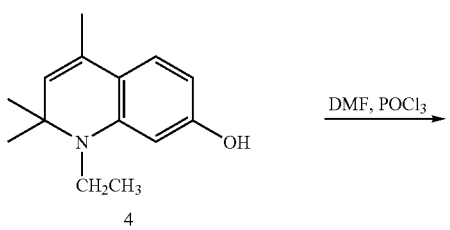
4

DMF, POCl₃
———————→

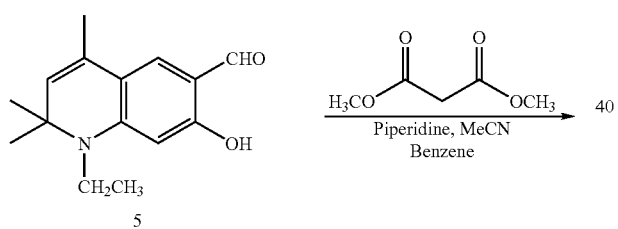
5

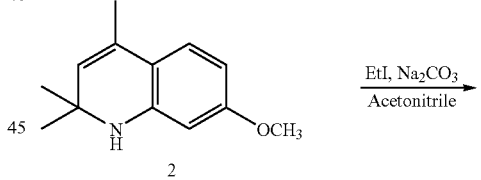
Piperidine, MeCN
Benzene
———————→

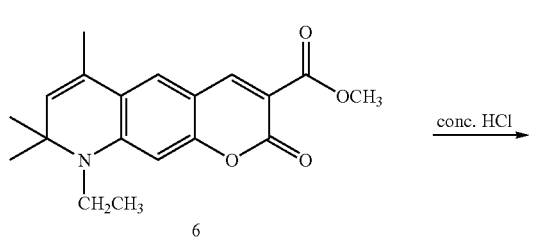
6 conc. HCl
———————→

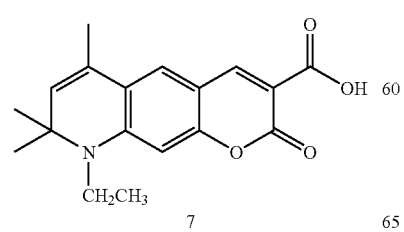
7

(1) Synthesis of 7-methoxy-2,2,4-trimethyl-1,2-dihydroquinoline (2)

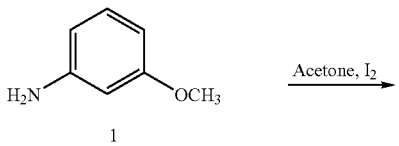
1

Acetone, I₂
———————→

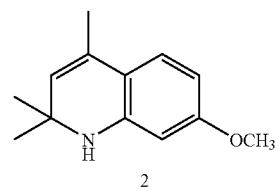
2

To a 200 ml two-necked flask, 5.0 g (40.63 mmol) of 3-methoxyaniline (1), 0.1 g of iodine and 100.0 ml of acetone were added, and the mixture was heated to reflux under nitrogen gas flow for 2 days. After evaporation of the solvent under reduced pressure, the reaction mixture was dissolved in methylene chloride, and then washed with saturated saline. The resultant was washed with anhydrous sodium sulfate and the solvent was evaporated under reduced pressure. The residue was purified by column chromatography (SiO₂, n-hexane:ethyl acetate=1:1 v/v) to obtain the desired compound.

(2) Synthesis of 9-azatricyclo[7.3.1.0<5,13>trideca-1(13),2,4-triene-2,6,12-triol (3)

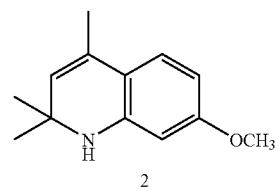
2

EtI, Na₂CO₃
———————→
Acetonitrile

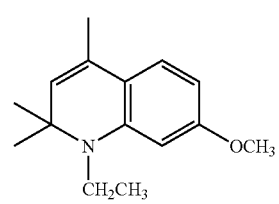
3

To a 200 ml two-necked flask, 2.0 g (9.85 mmol) of Compound 2, 100.0 ml of acetonitrile, 1.56 g (10.0 mmol) of ethyl iodide and 1.06 g (10.0 mmol) of sodium carbonate were added, and the mixture was heated to reflux for 2 days. After removing sodium carbonate by filtration, the filtrate was concentrated under reduced pressure. Ethyl acetate was added to the reaction mixture and the resulting mixture was washed with saturated saline. The resultant was dried over anhydrous sodium sulfate and the solvent was evaporated under reduced pressure. The residue was purified by column chromatography (SiO$_2$, n-hexane:ethyl acetate=5:1 v/v) to obtain the desired compound.

(3) Synthesis of 1-ethyl-2,2,4-trimethyl-1,2-dihydroquinoline-7-ol (4)

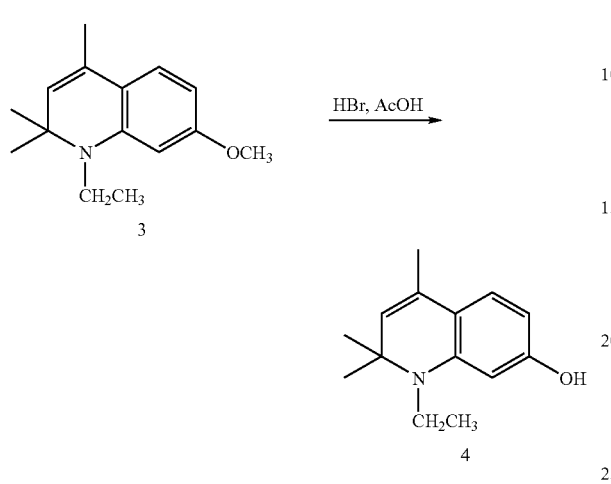

To a 100 ml eggplant type flask, 1.0 g (4.32 mmol) of Compound 3, 2.0 ml of hydrobromic acid and 20 ml of acetic acid were added, and the mixture was heated to reflux for 24 hours. The reaction solution was poured into cold water, and sodium hydroxide was added to make the mixture neutral, followed by extraction with methylene chloride. The organic layer was washed with water and then dried over anhydrous sodium sulfate. The solvent was evaporated under reduced pressure, and the residue was purified by column chromatography (SiO$_2$, n-hexane:ethyl acetate=2:1) to obtain the desired compound.

(4) Synthesis of 1-ethyl-7-hydroxy-2,2,4-trimethyl-1,2-dihydroquinoline-6-carboaldehyde (5)

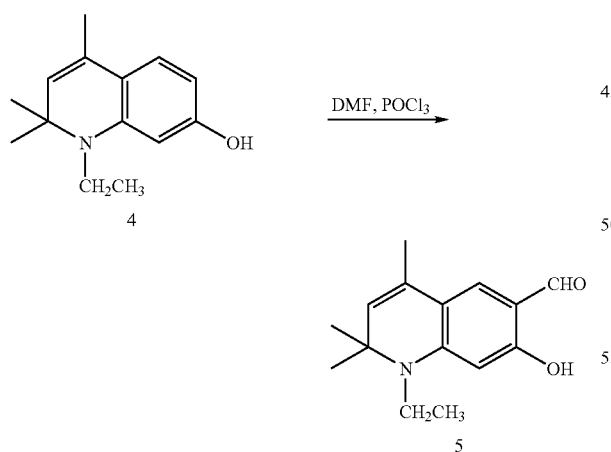

To a 100 ml flask, 1.0 g (4.60 mmol) of Compound 4 30.0 ml of dry DMF and 0.76 g (5.00 mmol) of POCl$_3$ were added, and the mixture was stirred at room temperature for 24 hours under nitrogen gas flow. After evaporation of the solvent under reduced pressure, the reaction mixture was dissolved in ethyl acetate and then washed with water. The resultant was dried over anhydrous sodium sulfate and the residue was purified by column chromatography (SiO$_2$, n-hexane:ethyl acetate=1:1) to obtain the desired product.

(5) Synthesis of methyl-5-ethyl-6,6,8-trimethyl-3-oxo-4,5,6-trihydro-5-aza-4-oxanthracene-2-carboxylate (6)

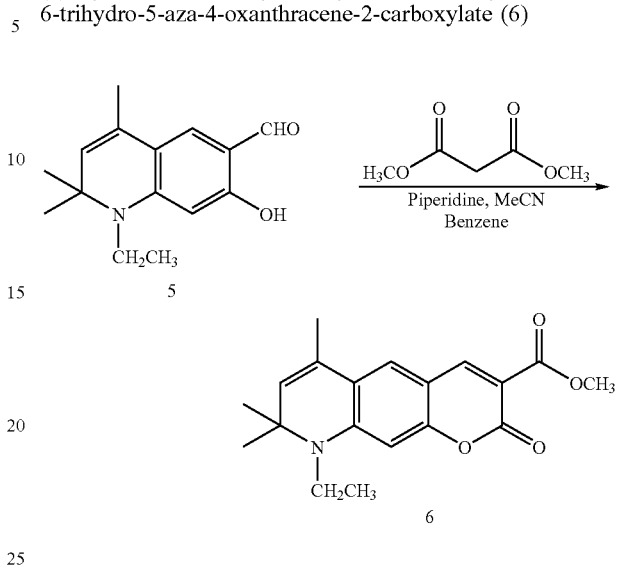

To a 100 ml two-necked flask, 1.0 g (4.08 mmol) of Compound 5, 0.54 g (4.08 mmol) of dimethyl malonate, 0.35 g (4.08 mmol) of piperidine, 35.0 ml of benzene and 15.0 ml of acetonitrile were added, and the mixture was heated to reflux under nitrogen gas flow for 4 hours. After evaporation of the solvent, the reaction mixture was dissolved in ethyl acetate and then washed with saturated saline. The resultant was dried over anhydrous sodium sulfate and the solvent was evaporated under reduced pressure. The residue was purified by column chromatography (SiO$_2$, n-hexane:ethyl acetate=5:1 v/v) to obtain the desired compound.

(6) Synthesis of 5-ethyl-6,6,8-trimethyl-3-oxo-4,5,6-trihydro-5-aza-4-oxanthracene-2-carboxylic acid (7)

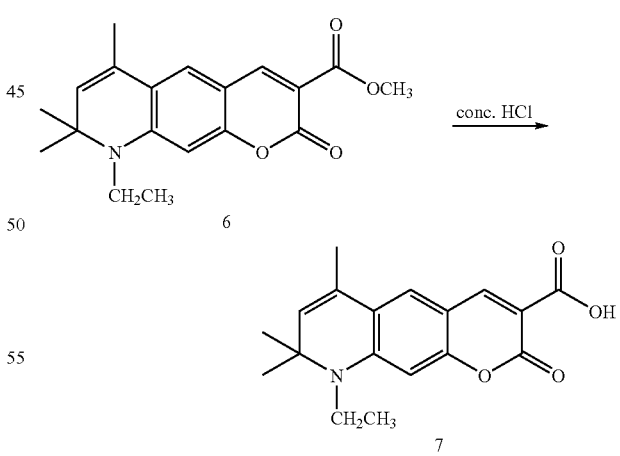

To a 20 ml of two-necked flask, 1.0 g (3.06 mmol) of Compound 6 and 10.0 ml of conc. hydrochloric acid were added, and the mixture was stirred at room temperature for 24 hours. The reaction solution was poured into cold water and the resultant was extracted with methylene chloride. The organic layer was washed with water and then dried over anhydrous sodium sulfate. The solvent was evaporated Example 7
Synthesis of Compound 9
In accordance with the following reaction scheme, Compound 9 shown in the reaction scheme was synthesized.
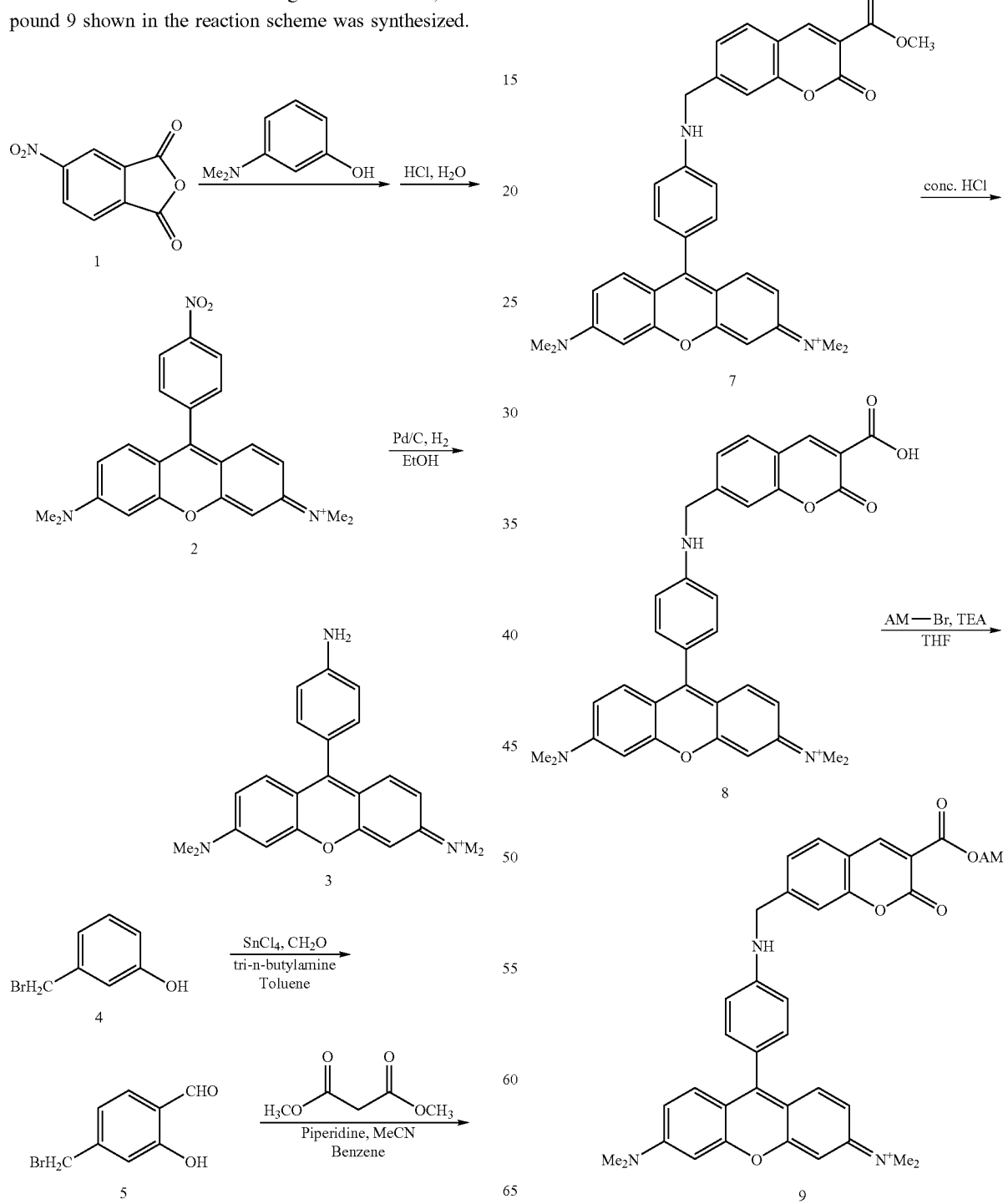

(1) Synthesis of Compound 2

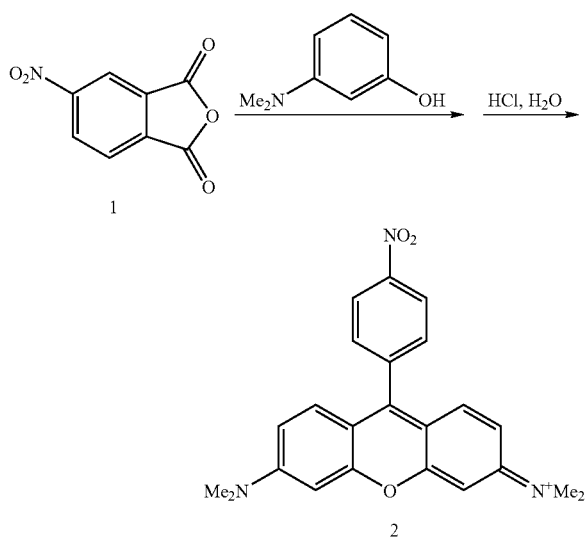

To a 20 ml eggplant type flask, 2.95 g (10.0 mmol) of Compound 1 and N,N-diethyl-3-aminophenol were added, and the mixture was stirred at 180° C. for 2 hours. After allowing the mixture to cool, 2M hydrochloric acid solution was added, and the resulting mixture was heated to reflux for 2 hours. After neutralizing the mixture with aqueous sodium hydroxide solution, the precipitates were recovered and purified by column chromatography (SiO$_2$, CH$_2$Cl$_2$) to obtain the desired compound.

(2) Synthesis of Compound 3

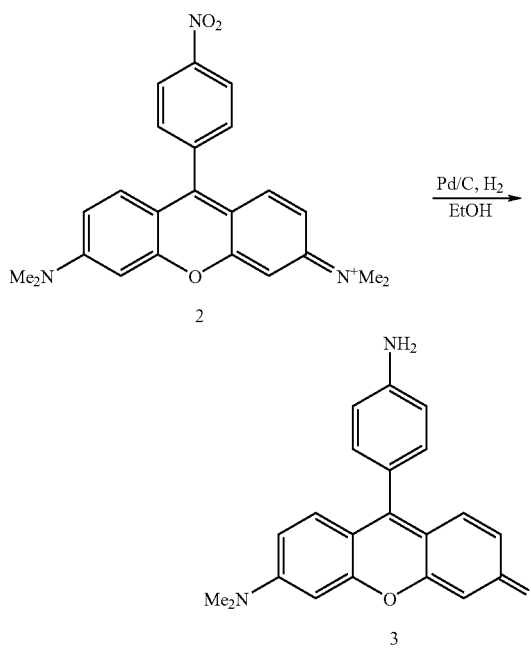

To a 50 ml two-necked flask, 0.40 g(0.58 mmol) of Compound 2, 50 ml of ethanol and 0.10 g of Pd/C were added, and the mixture was stirred at room temperature under hydrogen gas atmosphere for 2 hours. After removing Pd/C by filtration, the solvent was evaporated under reduced pressure and the residue was purified by column chromatography (SiO$_2$, CH$_2$Cl$_2$:MeOH=10:1 v/v) to obtain the desired compound.

(3) Synthesis of Compound 5

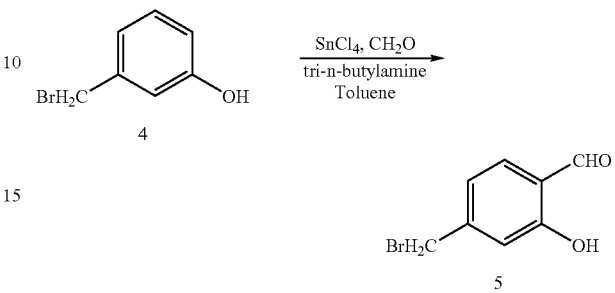

To a 50 ml two-necked flask, 1.0 g (5.78 mmol) of Compound 4, 10.0 ml of toluene and 0.43 g (2.31 mmol) of tri-n-butylamine were added, and the mixture was stirred in an ice bath under nitrogen gas flow. To the mixture, 0.14 g(0.57 mmol) of SnCl$_4$ was added, and the resulting mixture was stirred at room temperature for 30 minutes. To the mixture, 0.40 g (11.56 mmol) of paraformaldehyde was added and the resulting mixture was stirred at 100° C. for 12 hours. The reaction solution was poured into reaction solution and the resultant was made acidic with 1N HCl, followed by extraction with ether. After washing the organic layer with saturated saline, the resultant was dried over anhydrous sodium sulfate. The solvent was evaporated under reduced pressure, and the residue was purified by column chromatography (SiO$_2$, n-hexane:ethyl acetate=10:1 v/v) to obtain the desired compound.

(4) Synthesis of Compound 6

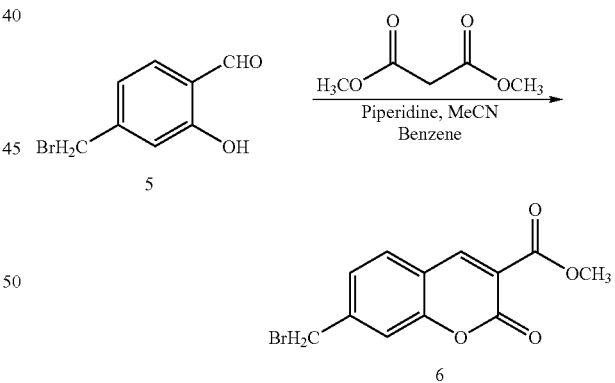

To a 100 ml eggplant type flask, 1.0 g (5.38 mmol) of Compound 5, 0.71 g (5.38 mmol) of dimethyl malonate, 0.46 g (5.38 mmol) of piperidine, 35.0 ml of benzene and 15.0 ml of acetonitrile were added, and the mixture was heated to reflux under nitrogen gas flow for 4 hours. After evaporation of the solvent under reduced pressure, the reaction mixture was dissolved in methylene chloride and then washed with water. After drying the resultant over anhydrous sodium sulfate, the solvent was evaporated under reduced pressure, and the residue was purified by column chromatography (SiO$_2$, CH$_2$Cl$_2$:AcOEt=2:1) to obtain the desired compound.

(5) Synthesis of Compound 7

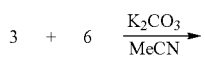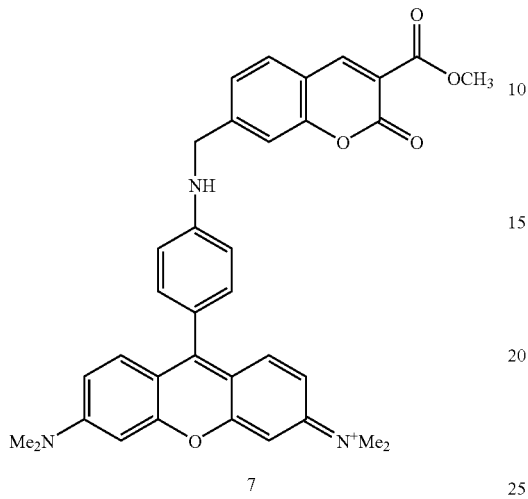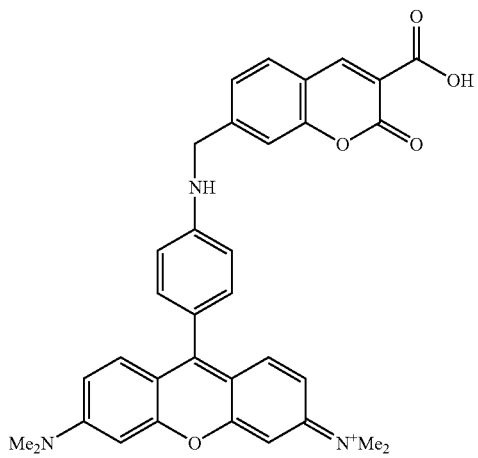

To a 100 ml three-necked flask, 0.50 g (1.39 mmol) of Compound 3, 0.41 g (1.39 mmol) of Compound 6, 0.69 g (5.00 mmol) of potassium carbonate and 50.0 ml of acetonitrile were added, and the mixture was heated to reflux under nitrogen gas flow for 24 hours. After removing potassium carbonate by filtration, the solvent was evaporated under reduced pressure. After dissolving the reaction mixture in ethyl acetate, the mixture was washed with water and dried over anhydrous sodium sulfate. The solvent was evaporated under reduced pressure and the residue was purified by column chromatography (SiO$_2$, CH$_2$Cl$_2$:MeOH=10:1 v/v) to obtain the desired compound.

(6) Synthesis of Compound 8

To a 50 ml eggplant type flask, 0.50 g (0.89 mmol) of Compound 7 and 20.0 ml of conc. hydrochloric acid were added, and the mixture was stirred at room temperature for 24 hours. The reaction solution was poured into cold water, and the resultant was extracted with methylene chloride. The organic layer was washed with water and then dried over anhydrous sodium sulfate. The solvent was evaporated under reduced pressure and the residue was purified by column chromatography (SiO$_2$, CH$_2$Cl$_2$:MeOH=50:1 v/v) to obtain the desired compound.

(7) Synthesis of Compound 9

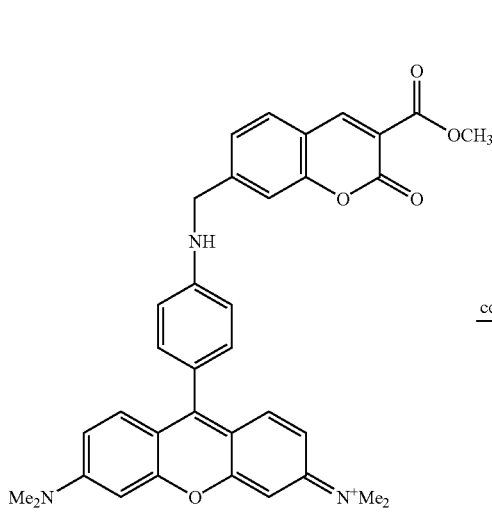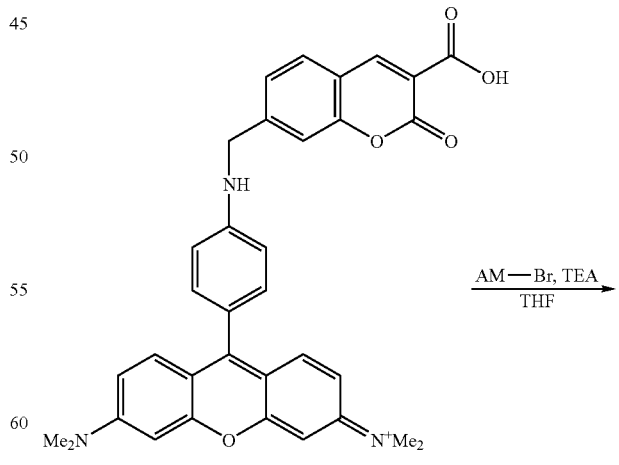

-continued

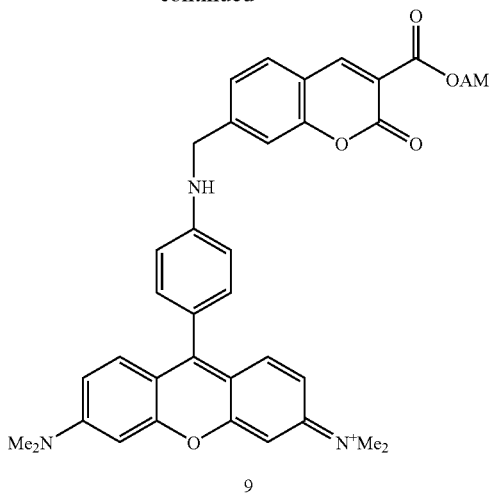

9

To a 100 ml three-necked flask, 0.50 g (0.89 mmol) of Compound 8, 20.0 ml of THF and 0.10 g (0.90 mmol) of triethylamine were added, and the flask was immersed in an ice bath. To the mixture, 0.16 g (0.90 mmol) of acetoxymethyl bromide was added, and the resulting mixture was stirred in the ice bath for 30 minutes and then at room temperature for 24 hours. After evaporation of the solvent under reduced pressure, the reaction mixture was dissolved in methylene chloride, and then washed with water. The resultant was dried over anhydrous sodium sulfate and the solvent was evaporated under reduced pressure. The residue was purified by column chromatography by a large thin layer chromatography ($SiO_2$, $CH_2Cl_2$:MeOH=20:11 v/v) to obtain the desired compound.

Example 8

Measurement of Magnesium Ions in Cells Using Fluorescent Probe (No. 1)

Magnesium ions in cells were measured using the fluorescent probe KMG-20 synthesized in Example 1. Since the fluorescent probe KMG-20 has an acetoxymethyl group, it has a high lipid solubility and is easy to transfer from the culture medium to the cell membrane. In the vicinity of the cell membrane, the acetoxymethyl group is removed by an ester hydrolysis enzyme in the cell and becomes again a water-soluble compound having a carboxyl group, so that it is diffused into the cytoplasm. Upon forming a complex with a magnesium ion, the fluorescence of KMG-20 is increased.

A solution of the fluorescent probe KMG-20 in DMSO (1.0 ml) was added to Hanks-HEPES buffer so as to attain a final concentration of 10.0 μM, and the mixture was subjected to ultrasonication. The culture medium in which bovine vascular endothelial cells had been cultured at 37° C. on a petri dish was replaced with the above-described KMG-20 solution, and the cells were incubated at 37° C. for 30 minutes. The culture medium was then replaced with a fresh buffer, and the cells were observed with a fluorescence microscope AxiovertS 100 at 20× magnification. The excitation wavelength was 440 nm and the detection wavelength was 500–530 nm. For comparison, the cells before the treatment with the fluorescent probe were also observed with the fluorescence microscope.

As a result, fluorescence was not observed before the treatment with the fluorescent probe, while in the cells after treatment with the fluorescent probe, it was observed that the fluorescent probe was uniformly dispersed and stained the cells. Further, in all of the cells, parts having a lower fluorescence intensity were observed. The part corresponds to the nucleus of the cell, and it was found that the probe was located in the vicinity of the nucleus, which surrounds the nucleus.

To clarify the behavior of free magnesium ions in the cells, 5 μM carbonylcyanoid p-(trifluoromethoxy)phenylhydrazone (FCCP) was added. As a result, the entire cell was brightened. The change in the fluorescence intensity with time after the addition of FCCP was observed. As a result, it was observed that the fluorescence intensity was increased during 1 minute from the addition of FCCP, and the fluorescence intensity thereafter was almost constant. The observed relationship between the time (minute) and the fluorescence intensity is shown in FIG. 1. It is known that magnesium ion usually binds to an oxygen atom in the phosphoric acid ester moiety of a phosphorylated substrate such as ATP, ADP, phosphorylated saccharide, nucleic acid or the like to neutralize the electric charge thereof, and serves as an acid catalyst, and that enzymes whose corresponding substrates are phosphoric acid ester compounds require magnesium ion as a co-factor. Since FCCP serves as a respiration inhibitor of mitochondria in the cells, the ATP activity in the cells is decreased and so the free magnesium ion level is increased, it is thought that KMG-20 formed a complex with magnesium ion, thereby increasing the fluorescence intensity.

Further, 10 μM acetylcholine was added to the cells so as to compulsively increase the calcium level in the cells. As a result, increase of the fluorescence intensity was not observed. From this, it was proved that KMG-20 may be used to selectively measure magnesium ions sufficiently even in the presence of calcium ions.

Example 9

Measurement of Magnesium Ions in Cells Using Fluorescent Probe (No. 2)

Behavior of magnesium ions in cells were measured using the fluorescent probe synthesized in Example 4.

Since this fluorescent probe KMG-20 has an acetoxymethyl group, it has a high lipid solubility and is easy to transfer from the culture medium to the cell membrane. In the vicinity of the cell membrane, the acetoxymethyl group is removed by an ester hydrolysis enzyme in the cell and becomes again a water-soluble compound having a carboxyl group, so that it is diffused into the cytoplasm.

A solution of the fluorescent probe in DMSO (1.0 ml) was added to Hanks-HEPES buffer so as to attain a final concentration of 10.0 μM, and the mixture was subjected to ultrasonication. The culture medium in which PC-12 cells (cloned nerve cells isolated from rat adrenal medulla chrome-philic cytoma) had been cultured at 37° C. on a petri dish was replaced with the fluorescent probe solution, and the cells were incubated at 37° C. for 30 minutes. The culture medium was then replaced with a fresh buffer, and the cells were observed with a fluorescence microscope AxiovertS 100. The excitation wavelength was 440 nm and the detection wavelength was 500–530 nm. For comparison, the cells before the treatment with the fluorescence probe were also observed with the fluorescence microscope.

As a result, fluorescence was not observed before the treatment with the fluorescent probe, while in the cells after treatment with the fluorescent probe, it was observed that the fluorescent probe was uniformly dispersed and stained the cells. Further, in all of the cells, parts having a lower fluorescence intensity were observed. The part corresponds to the nucleus of the cell, and it was found that the probe was located in the vicinity of the nucleus, which surrounds the nucleus.

To clarify the behavior of free magnesium ions in the cells, 5.0 μM carbonylcyanoid p-(trifluoromethoxy)phenyl-hydrazone (FCCP) was added. As a result, the entire cell was brightened. The change in the fluorescence intensity with time after the addition of FCCP was observed. As a result, it was observed that the fluorescence intensity was increased during 1 minute from the addition of FCCP, and the fluorescence intensity thereafter was almost constant. It is known that magnesium ion usually binds to an oxygen atom in the phosphoric acid ester moiety of a phosphorylated substrate such as ATP, ADP, phosphorylated saccharide, nucleic acid or the like to neutralize the electric charge thereof, and serves as an acid catalyst, and that enzymes whose corresponding substrates are phosphoric acid ester compounds require magnesium ion as a co-factor. Since FCCP serves as a respiration inhibitor of mitochondria in the cells, the ATP activity in the cells is decreased and so the free magnesium ion level is increased, it is thought that the fluorescent probe formed a complex with magnesium ion, thereby increasing the fluorescence intensity.

Further, 10 μM acetylcholine was added to the cells so as to compulsively increase the calcium level in the cells. As a result, increase of the fluorescence intensity was not observed. From this, it was proved that the newly developed fluorescent probe may be used to selectively measure magnesium ions sufficiently even in the presence of calcium ions.

Example 10

Selectivity to Magnesium Ion of Fluorescent Probes

Selectivities to magnesium ion (i.e., the ratio of binding constant to magnesium ion to the binding constant to calcium ion) of KMG-20 synthesized in Example 1 and KMG-27 synthesized in Example 4 were measured. More particularly, this measurement was carried out as follows:

The fluorescent indicator was dissolved in a solvent (HEPES 10.0 mM, KCl 120.0 mM, NaCl 20.0 mM, EGTA 2.0 mM, pH 7.20) to a concentration of 10 μM. To this solution, a metal salt solution ($MgCl_2$, $CaCl_2$) in the above-described solvent was added to a concentration of 0 to 500 mM, and fluorescence spectrum was measured.

The conditions of the fluorophotometer (Hitachi F4500) were as follows: excitation wavelength: 448 nm, slit width: excitation side: 2.5 nm, fluorescence side 2.5 nm, photomultiplier voltage: 700V, scanning rate: 240 nm/min.

The fluorescence intensities at the maximum fluorescence wavelength (505 nm) when the concentration of the metal ion was changed were measured, and the binding constants to $Mg^{2+}$ and $Ca^{2+}$ were calculated by using Benesi-Hildebrand plot method (J. Am. Chem. Soc. 71, 2703 (1949)). The results are shown in Table 1 below.

For comparison, the binding constants of known magnesium probes commercially available from Molecular Probes, that is, mag-fura-2 (Proc. Natl. Acad. Sci. USA, 86, 2981 (1989)), mag-indo-1(J. Physiol, 475, 319 (1994)), mag-fura-5 (J. Physiol, 475, 319 (1994)) and Magnesium Green (J. Biol. Chem. 270, 18975 (1995)) are also shown in Table 1.

TABLE 1

| | Probe | $K_{Mg}(M^{-1})$ | $K_{Ca}(M^{-1})$ | $K_{Mg}/K_{Ca}$ |
|---|---|---|---|---|
| Examples | KMG-20 | 100.0 | 33.3 | 3.0 |
| | KMG-27 | 102.0 | 33.0 | 3.09 |
| Comparative | mag-fura-2 | 526.3 | 40,000 | 0.013 |
| Examples | mag-indo-1 | 370.4 | 28,570 | 0.013 |
| | mag-fura-5 | 434.8 | 35,710 | 0.012 |
| | Magnesium Green | 500.0 | 166,660 | 0.003 |

As is apparent from Table 1, the selectivities to magnesium ion ($K_{Mg}/K_{Ca}$) of the fluorescent probes according to the present invention were not less than 200 times higher than those of the conventional magnesium ion probes.

INDUSTRIAL AVAILABILITY

The fluorescent probe according to the present invention is a selective fluorescent probe for measuring magnesium ion, which can selectively form a complex with magnesium ion in aqueous system even in the presence of calcium ions. It is thought that the fluorescent probe according to the present invention will much contribute to the analysis of behaviors of magnesium ions in the body or the like.

The invention claimed is:

1. A method for measuring magnesium ion in a sample, comprising the steps of:
    contacting a fluorescent probe, which has a structure represented by the following Formula [II']:

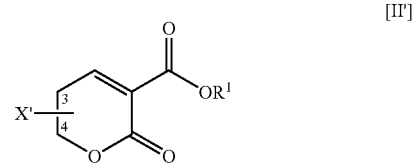

wherein $R^1$ represents a hydrogen atom, metal atom or an ester-forming group; and X' is a fluorescent group which may form a condensed ring together with carbon atom 3 and carbon atom 4; each hydrogen atom bound to arbitrary one or more carbon atoms constituting the ring structure in Formula [II'] may be substituted by $C_1$–$C_6$ alkyl, $C_1$–$C_6$ alkoxyl, amino, halogen or nitro, with a sample containing magnesium ions; and
    measuring an increase in fluorescence from said fluorescent probe bound to magnesium ion in said sample to indicate magnesium ion in the sample.

2. The method according to claim 1, wherein the fluorescent probe has a structure represented by the following Formula [III]:

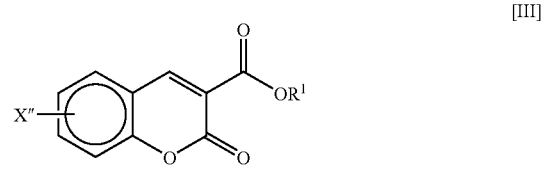

(wherein R[1] represents the same meaning as in said Formula [I]; X" is a fluorescent group which may be a ring condensed with the benzene ring shown in the formula; each hydrogen atom bound to arbitrary one or more carbon atoms constituting the ring structure in Formula [III] may be substituted by $C_1$–$C_6$ alkyl, $C_1$–$C_6$ alkoxyl, amino, mono- or dialkylamino in which each alkyl group has 1 to 6 carbon atoms, halogen or nitro).

3. The method according to claim 2, (wherein in Formula [III] R[1] represents the same meaning as in said Formula [I]; and X" is a fluorescent group which may be a ring condensed with the benzene ring shown in formula [III]), and further wherein each hydrogen atom bound to arbitrary one or more carbon atoms constituting the ring structure in Formula [III] is unsubstituted.

4. The method according to claim 2, wherein the fluorescent probe has a structure represented by the following Formula [IV]:

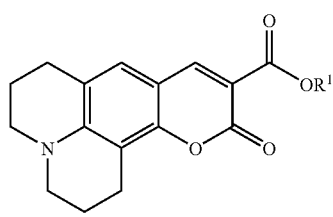

[IV]

(wherein R[1] represents the same meaning as in said Formula [I]; each hydrogen atom bound to arbitrary one or more carbon atoms constituting the ring structure in Formula [IV] may be substituted by $C_1$–$C_6$ alkyl, $C_1$–$C_6$ alkoxyl, amino, mono- or dialkylamino in which each alkyl group has 1 to 6 carbon atoms, halogen or nitro), or represented by the following Formula [V]:

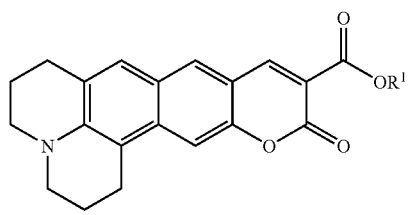

[V]

(wherein R[1] represents the same meaning as in said Formula [I]; each hydrogen atom bound to arbitrary one or more carbon atoms constituting the ring structure in Formula [V] may be substituted by $C_1$–$C_6$ alkyl, $C_1$–$C_6$ alkoxyl, amino, mono- or dialkylamino in which each alkyl group has 1 to 6 carbon atoms, halogen or nitro).

5. The method according to claim 4, wherein the fluorescent probe has the structure represented by said Formula [IV] or [V] (wherein R[1] represents the same meaning as in said Formula [I]), and further wherein each hydrogen atom bound to arbitrary one or more carbon atoms constituting the ring structure in Formula [III] is unsubstituted.

6. The method according to claim 2 or 3, wherein X" in Formula [III] is represented by the Formula [VI]:

X'''-Z-   [VI]

(wherein X''' represents a fluorescent group having a condensed ring containing 2 to 4 rings; -Z- represents a group which binds said fluorescent group and the benzene ring shown in said Formula [III]).

7. The method according to claim 6, wherein said X''' is represented by the Formula [VII]:

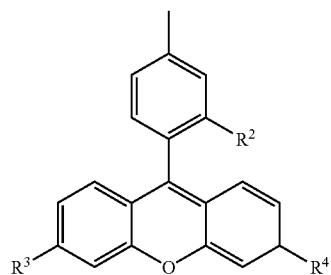

[VII]

(wherein $R^2$ represents a hydrogen atom or carboxyl, $R^3$ and $R^4$ independently represent hydroxyl. $C_1$–$C_6$ alkyl, or dialkylamino in which each alkyl group has 1 to 6 carbon atoms (the nitrogen atom therein may form a double bond with a carbon atom constituting the ring to form a quaternary amine).

8. The method according to claim 3, wherein the fluorescent probe is represented by the Formula [X]:

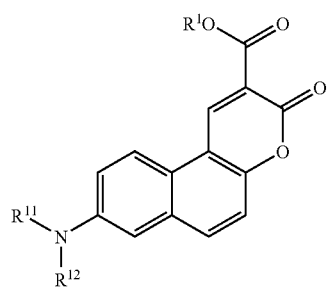

[X]

(wherein R[1] represents the same meaning as in said Formula [I]; $R^{11}$ and $R^{12}$ independently represent hydrogen, hydroxyl, halogen, $C_1$–$C_6$ alkyl, $C_1$–$C_6$ haloalkyl, $C_1$–$C_6$ alkoxyl, $C_1$–$C_6$ haloalkoxyl, benzyl or acetyl, or a group containing one or two monosaccharide structures or an acylate thereof).

9. The method according to claim 8, wherein said group containing one or two monosaccharide structures or an acylate thereof is glycosyl, glycoside, fructosyl, fructoside or a group represented by Formula [XI]:

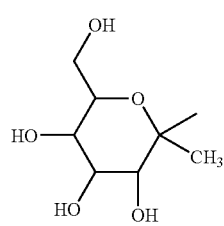

[XI]

with the proviso that 1 to 4 hydroxyl groups in these groups may be acylated with $C_1$–$C_6$ acyl group(s).

10. The method according to claim 8 or 9, wherein said monosaccharide structure is bound to the nitrogen atom in the Formula [X] through $C_1$–$C_6$ alkyl or $C_1$–$C_6$ alkoxyl group.

11. The method according to any one of claim 1, 8, or 9, wherein the $R^1$ in said Formula [I], [II], [III], [IV], [V], [VII] or [X] is represented by the following Formula [IX]:

(wherein $R^9$ represents $C_1$–$C_4$ alkylene, and $R^{10}$ represents $C_1$–$C_4$ alkyl).

12. The method according to claim 11, wherein the $R^9$ in said Formula [IX] is methylene group and $R^{10}$ in said Formula [IX] is methyl group.

13. The method according to claim 4, wherein the fluorescent probe is represented by Formula [XIII]:

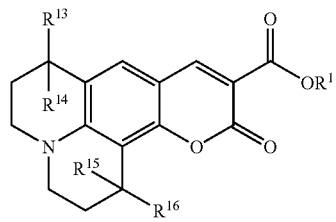

(wherein $R^1$ represents the same meaning as in Formula $R^{13}$, $R^{14}$, $R^{15}$, and $R^{16}$ independently represent hydrogen, $C_1$–$C_5$ alkyl or halogen (excluding the cases wherein $R^{13}$, $R^{14}$, $R^{15}$ and $R^{16}$ are simultaneously hydrogen atoms).

14. The method according to claim 4, wherein the fluorescent probe which is represented by the Formula [XIV]:

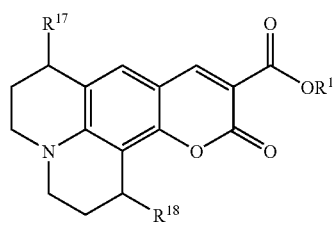

(wherein $R^1$ represents the same meaning as in Formula [I]; and $R^{17}$ and $R^{18}$ independently represent hydrogen, hydroxyl, halogen, carboxyl or —COOR$^{19}$ (wherein $R^{19}$ represents a monovalent metal ion) (excluding the cases wherein $R^{17}$ and $R^{18}$ are simultaneously hydrogen atoms).

15. The method according to claim 2, wherein the fluorescent probe is represented by the Formula [XV]:

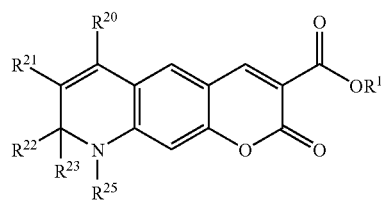

(wherein $R^1$ represents the same meaning as in Formula [I]; and $R^{20}$, $R^{21}$, $R^{22}$, $R^{23}$, and $R^{25}$ independently represent hydrogen, $C_1$–$C_5$ alkyl, halogen or hydroxyl).

16. The method according to claim 6, wherein said Formula [VI]

$$X'''-Z-\quad\quad [VI]$$

is represented by the Formula [XVI]:

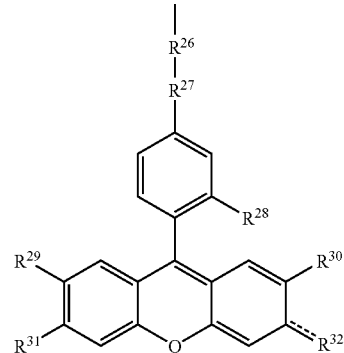

(wherein $R^{26}$ may or may not exist, when it exists, $R^{26}$ represents $C_1$–$C_5$ alkylene; $R^{27}$ represents —NH—, —NH—CO— or —OCO—; $R^{28}$ represents hydrogen, carboxyl or —COOR$^{33}$ (wherein $R^{33}$ represents a monovalent metal atom or $C_1$–$C_5$ alkyl); $R^{29}$ and $R^{30}$ independently represent hydrogen, $C_1$–$C_5$ alkyl or halogen; $R^{31}$ represents hydroxyl, $C_1$–$C_5$ alkyl or dialkylamino in which each alkyl group has 1 to 5 carbon atoms; the symbol "----" which binds $R^{32}$ and the ring represents single bond or double bond, in cases where it represents single bond, $R^{32}$ represents hydroxyl, $C_1$–$C_5$ alkyl, or dialkylamino in which each alkyl group has 1 to 5 carbon atoms; in cases where it represents double bond, $R^{32}$ represents carbonyl or =N$^+$R$^{34}$R$^{35}$ (wherein $R^{34}$ and $R^{35}$ independently represent $C_1$–$C_5$ alkyl).

17. The method according to claim 16, wherein in said Formula [XVI], $R^{26}$ is methylene, $R^{27}$ is —NH—, all of $R^{28}$, $R^{29}$ and $R^{30}$ are hydrogen atoms, $R^{31}$ is N(CH$_3$)$_2$, and $R^{32}$ is =N$^+$(CH$_3$)$_2$.

18. The method according to any one of claims 13 to 15, wherein $R^1$ in said Formula [XIII], [XIV], [XV] or [XVI] is represented by the Formula [IX]:

—R$^9$—OCO—R$^{10}$      [IX]

(wherein $R^9$ represents $C_1$–$C_4$ alkylene, and $R^{10}$ represents $C_1$–$C_4$ alkyl).

19. The method according to claim 18, wherein $R^9$ in said Formula [IX] is methylene and $R^{10}$ in said Formula [IX] is methyl.

20. The method according to claim 1, wherein said sample contains cells and said magnesium ions are contained in said cells.

* * * * *